US007988656B2

(12) United States Patent
Uesugi et al.

(10) Patent No.: US 7,988,656 B2
(45) Date of Patent: Aug. 2, 2011

(54) NATURAL ORIFICE MEDICAL OPERATION AND ENDOSCOPIC OVERTUBE

(75) Inventors: Takefumi Uesugi, Tokyo (JP); Kenji Noda, Tokyo (JP); Takayasu Mikkaichi, Tokyo (JP); Kunihide Kaji, Tokyo (JP); David E. Barlow, Coopersburg, PA (US)

(73) Assignee: Olympus Medical Systems Corp., Tokyo (JP)

( * ) Notice: Subject to any disclaimer, the term of this patent is extended or adjusted under 35 U.S.C. 154(b) by 767 days.

(21) Appl. No.: 11/653,145

(22) Filed: Jan. 12, 2007

(65) Prior Publication Data

US 2007/0255165 A1  Nov. 1, 2007

Related U.S. Application Data

(60) Provisional application No. 60/759,120, filed on Jan. 13, 2006.

(51) Int. Cl.
*A61M 37/00* (2006.01)
*A61B 19/00* (2006.01)
*A61B 1/00* (2006.01)

(52) U.S. Cl. .......................... 604/23; 128/898; 600/114

(58) Field of Classification Search ................. 604/523; 600/104, 114
See application file for complete search history.

(56) References Cited

U.S. PATENT DOCUMENTS

| 5,382,231 | A  | * | 1/1995  | Shlain ........................... 128/898 |
| 5,458,131 | A  | * | 10/1995 | Wilk ............................. 600/105 |
| 6,412,493 | B1 | * | 7/2002  | Hsue ............................ 128/898 |
| 7,179,267 | B2 | * | 2/2007  | Nolan et al. .................. 606/153 |
| 2005/0119617 | A1 | * | 6/2005 | Stecker et al. ................ 604/104 |
| 2005/0222491 | A1 |   | 10/2005 | Noda et al. |
| 2005/0234391 | A1 | * | 10/2005 | Uesugi et al. ................. 604/24 |
| 2007/0157937 | A1 | * | 7/2007  | Mikkaichi et al. ............ 128/898 |
| 2007/0255100 | A1 |   | 11/2007 | Barlow et al. |
| 2008/0108871 | A1 | * | 5/2008  | Mohr ............................ 600/114 |

FOREIGN PATENT DOCUMENTS

| JP | 2005-287839 | 10/2005 |
| JP | 2005-287840 | 10/2005 |

* cited by examiner

*Primary Examiner* — Nicholas D Lucchesi
*Assistant Examiner* — Ian K Holloway
(74) *Attorney, Agent, or Firm* — Scully, Scott, Murphy & Presser, P.C.

(57) ABSTRACT

In order to control the pressure in an abdominal cavity of a patient and a pressure in a hollow organ, a medical system includes: a first pressure sensor for measuring the pressure of a gas in the abdominal cavity; a first port for insufflating and evacuating the abdominal cavity; a second pressure sensor for measuring the pressure of a gas in the hollow organ; a second port for insufflating and evacuating the hollow organ; an air supply apparatus connected to the second port for controlling the air supply and evacuation based on the output by the first and second pressure sensors; a third port connected to the second pressure sensor in the air supply apparatus; an endoscope connected to the air supply apparatus; a pneumoperitoneum needle connected to the first port; and a puncture needle connected to the second port.

15 Claims, 30 Drawing Sheets

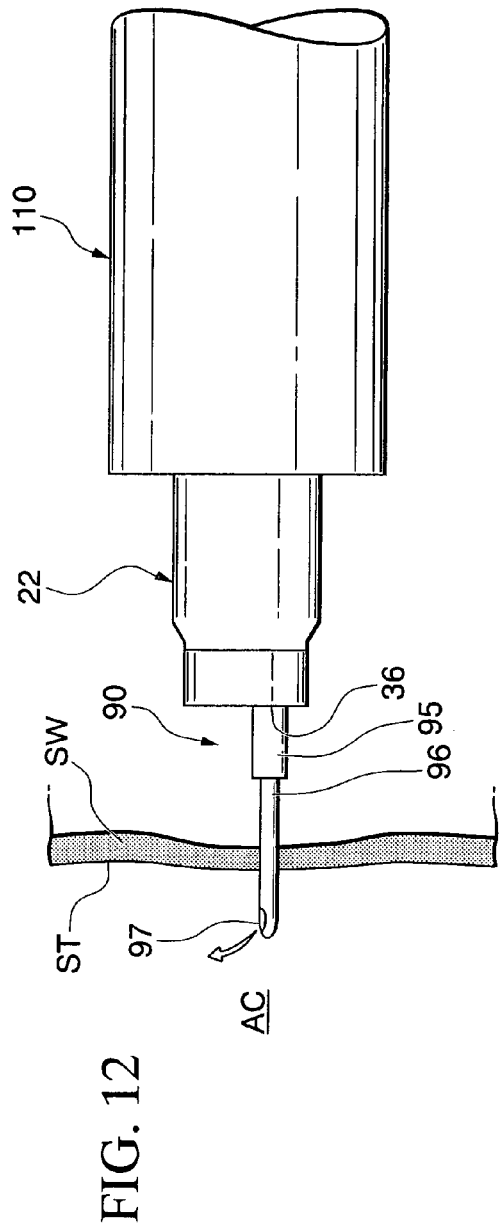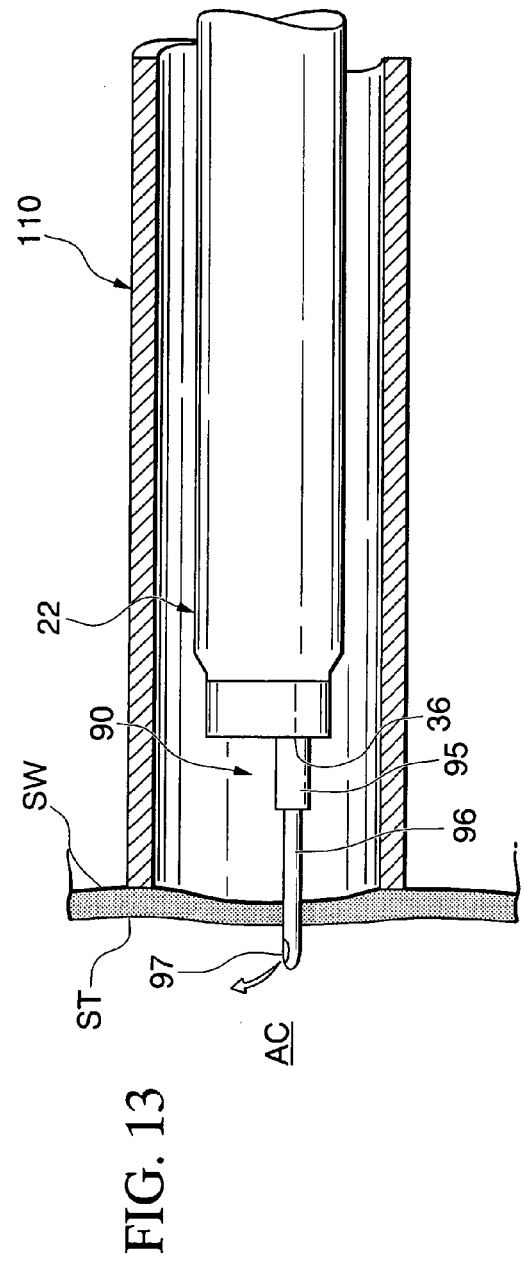

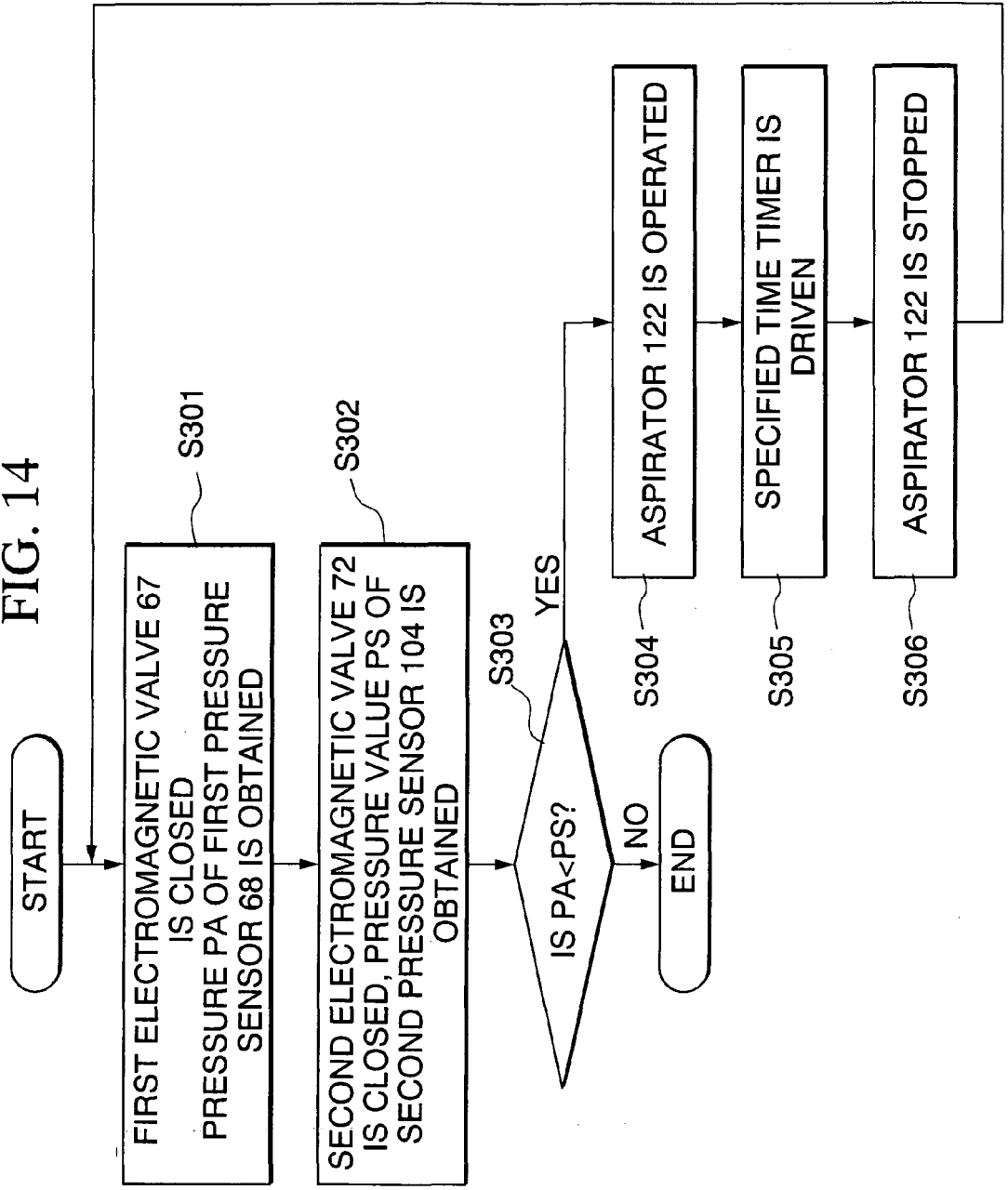

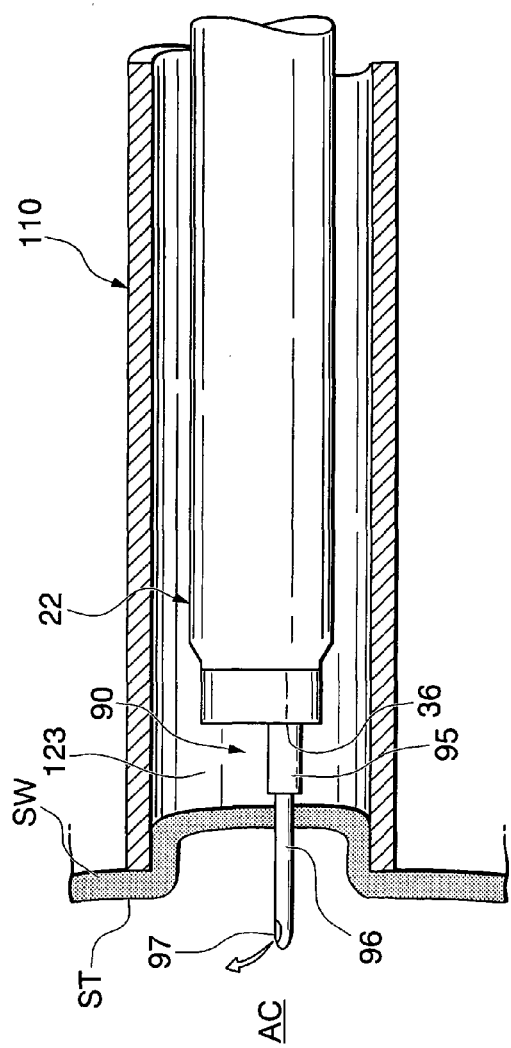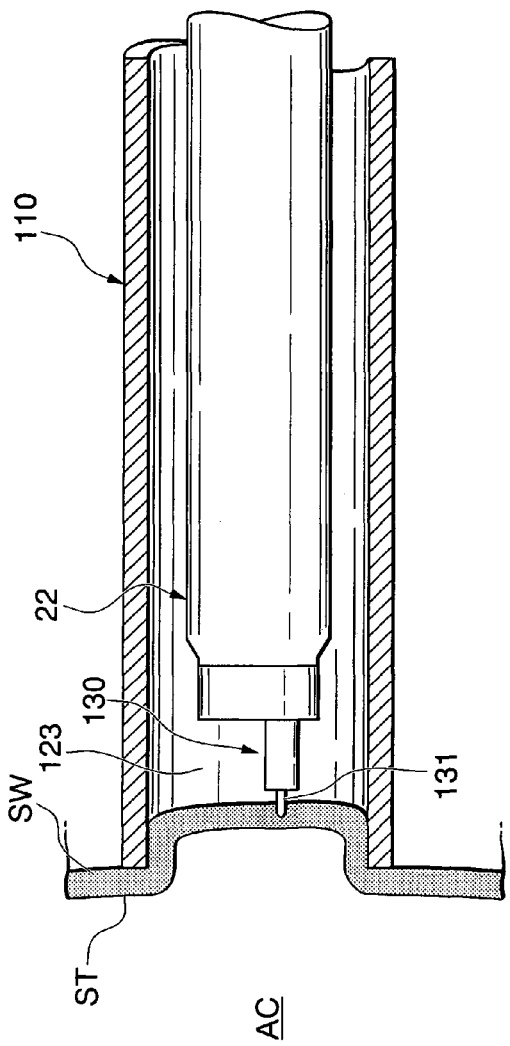
FIG. 15
FIG. 16

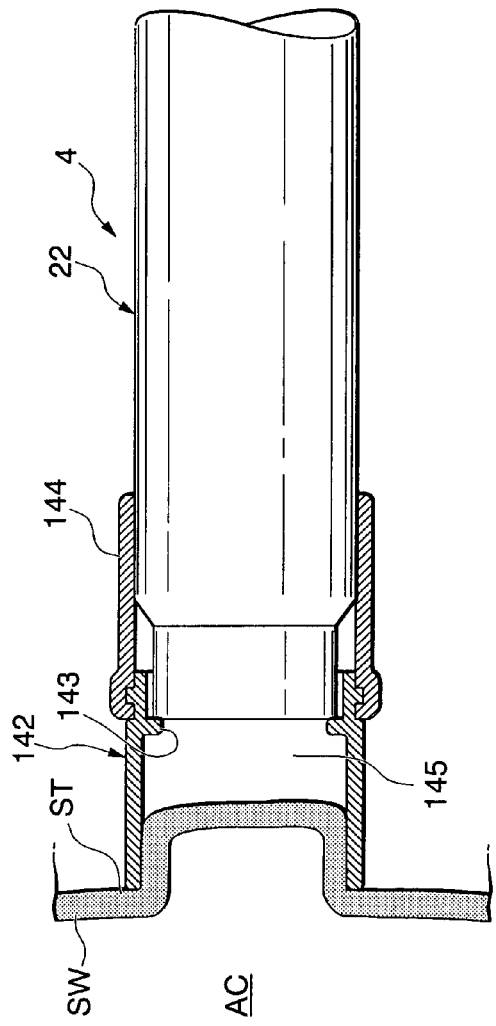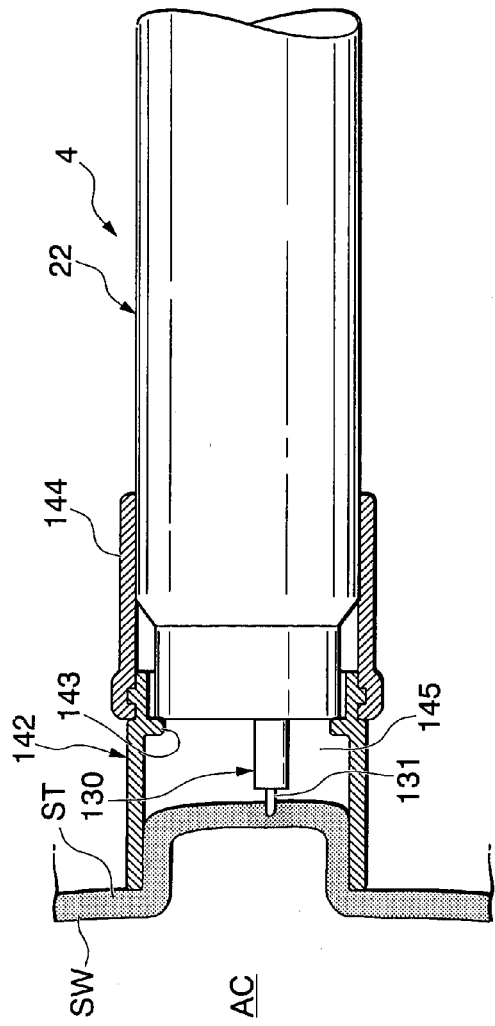

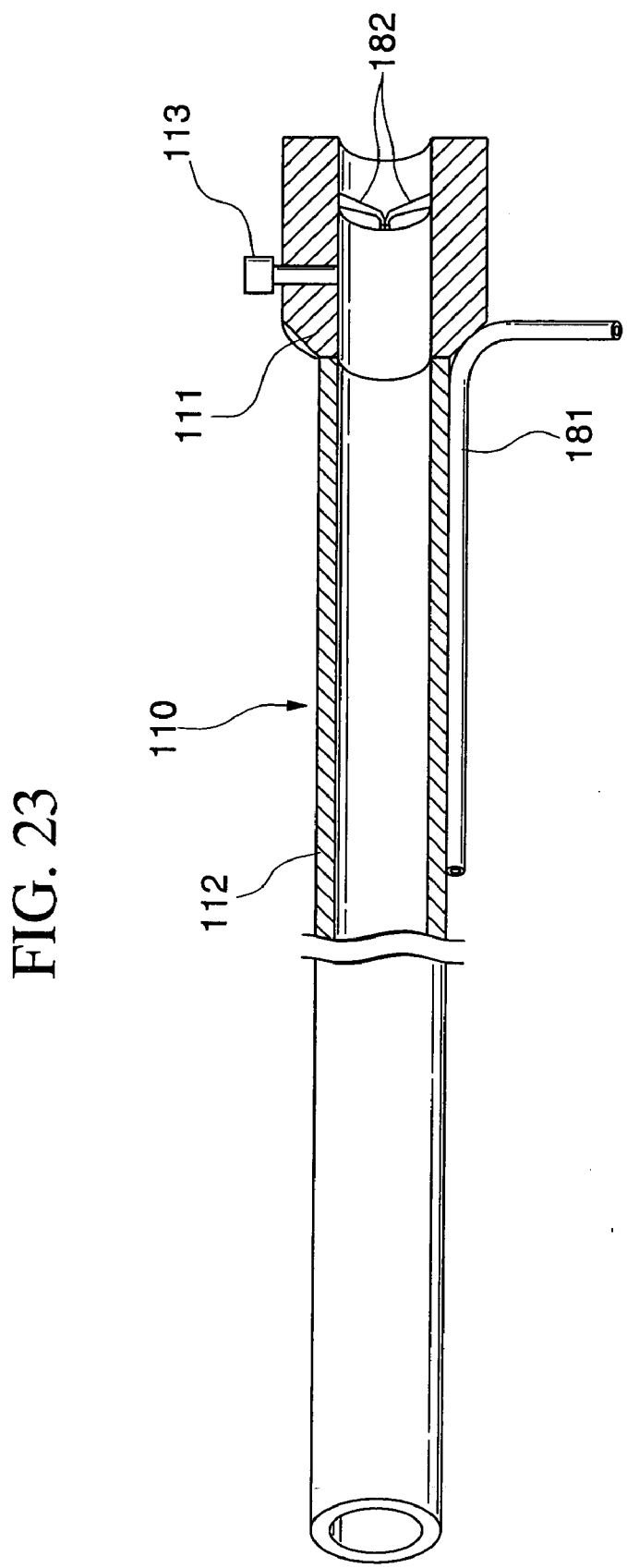

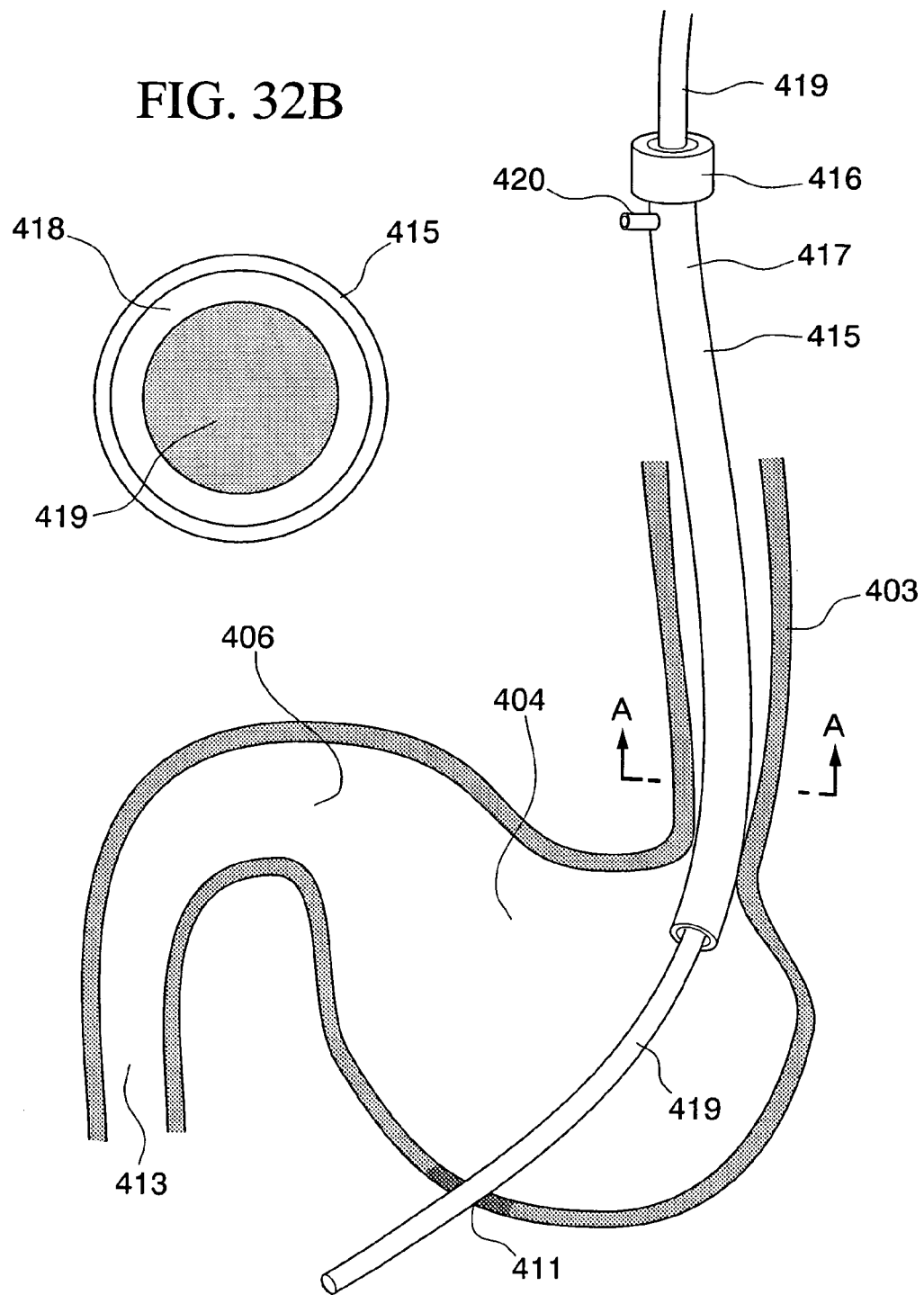

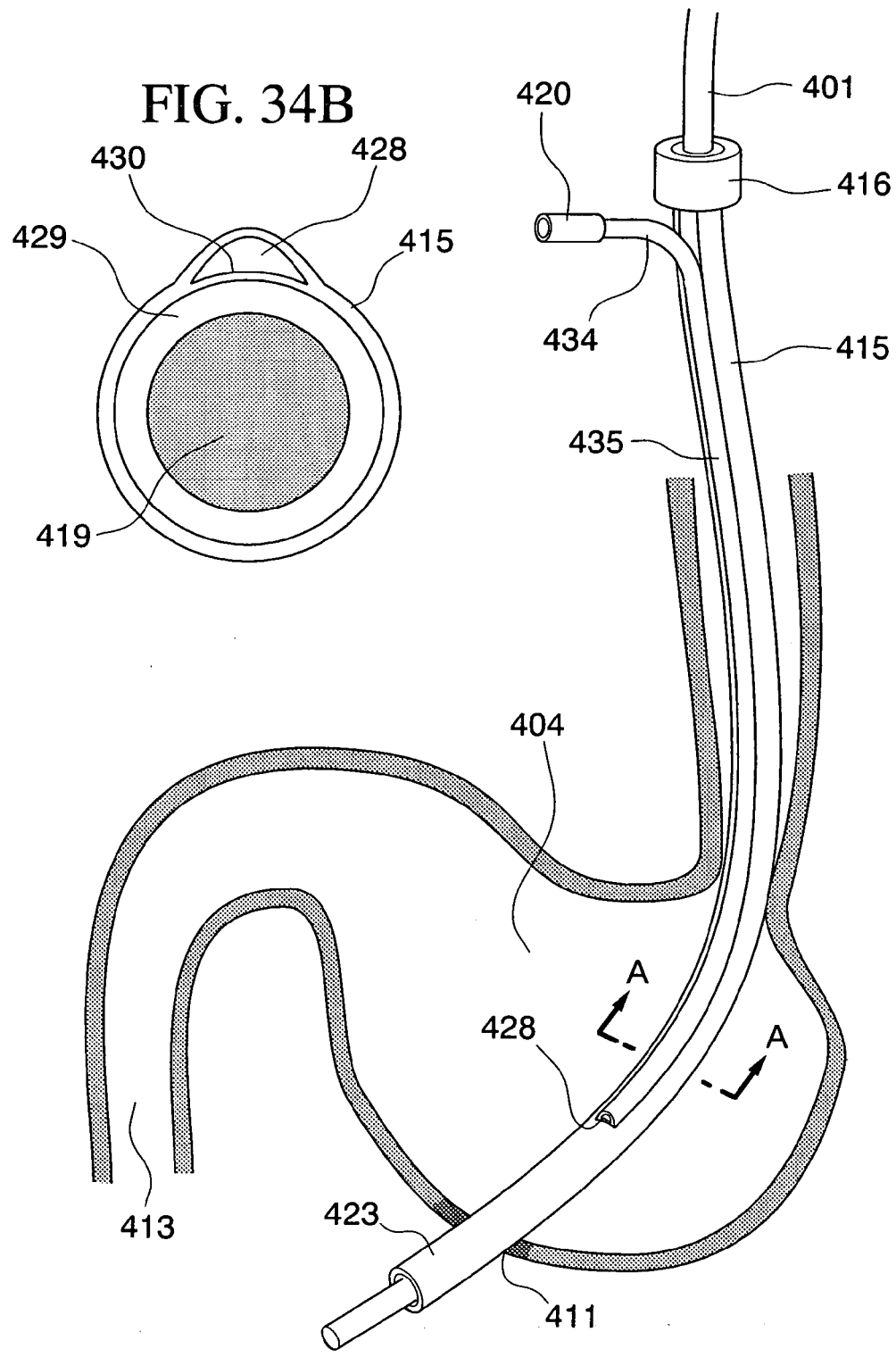

NATURAL ORIFICE MEDICAL OPERATION AND ENDOSCOPIC OVERTUBE

CROSS-REFERENCE TO RELATED APPLICATION

The present application claims priority on U.S. patent application Ser. No. 11/331,974, filed Jan. 13, 2006, and U.S. provisional application No. 60/759,120, filed Jan. 13, 2006, the contents of which are incorporated herein by reference.

BACKGROUND OF THE INVENTION

1. Field of the Invention

The present invention relates to a method for accessing the abdominal cavity and a medical operation via a natural orifice. Also, the present invention relates to an endoscopic system and an overtube.

2. Description of the Related Art

In the case of accomplishing medical intervention (including observation and treatment and the like; as applied hereafter) to the viscera of the human body, in lieu of cutting deeply into the abdominal wall, surgery in which multiple openings are cut into the abdominal wall, through which are respectively inserted such medical devices as rigid laparoscopes, and forceps and the like, is well-known. Since this is accomplished with only small openings, there is the advantage of minimal invasion and the rapid recovery of the patient.

In recent years, as a method of further reducing the invasion of the patient, it has been proposed that operations be accomplished by inserting an endoscope through such natural orifices as the patient's mouth, a nostril, or anus. An example of such a medical operation is disclosed in U.S. Pat. No. 5,458,131. By inserting a flexible endoscope from the mouth of a patient in which insufflation of the abdomen has been initiated, the endoscope can then be sent to the abdominal cavity through an opening formed in the stomach wall, and used to monitor the inside of the abdominal cavity. Furthermore, organs can be treated using treatment devices passed through the endoscope, or through other openings to the stomach, or from the opening in the Sigmoid colon formed from the anus, and upon completion of the operation within the abdominal cavity, the treatment devices can be removed and the openings closed. At the time of closing the openings, the tissue can be aspirated by binding the periphery of the opening, and constraining it with an O ring.

SUMMARY OF THE INVENTION

An object of the present invention relates to performing a medical operation for approaching the inside of the abdominal cavity by forming an opening in the wall of a hollow organ from the natural orifice of the body, and provides a method for accomplishing a medical operation by appropriately controlling the pressure within the abdominal cavity and hollow organs.

A first aspect of the present invention provides a method for accessing the abdominal cavity. The method includes: introducing a first flow path into the abdominal cavity; introducing a second flow path into a hollow organ from a natural orifice of the living body; performing a pressure control so that a pressure within the hollow organ is lower than a pressure of the abdominal cavity by using of the first flow path and the second flow path; forming an opening in a wall of the hollow organ from the inside of the hollow organ when the pressure within the hollow organ is equal to or less than the pressure within the abdominal cavity, in the step of performing a pressure control; and inserting a device for performing a medical operation through the opening.

A second aspect of the present invention provides a medical operation accomplished through a natural orifice. The medical operation includes: introducing a first flow path into an abdominal cavity; introducing the second flow path into the hollow organ from the natural orifice of the living body; performing a pressure control using the first flow path and the second flow path so that a pressure within the hollow organ is equal to or less than a pressure of the abdominal cavity; and in a state in which, by performing a pressure control, the pressure within the hollow organ is made equal to or less than the pressure within the abdominal cavity, withdrawing the device which is inserted from the natural orifice of the living body and is introduced into the abdominal cavity through an opening formed in the hollow organ, from the abdominal cavity.

A third aspect of the present invention provides a medical system capable of controlling a pressure in an abdominal cavity of a patient and a pressure in a hollow organ. The system comprises: a first pressure sensor for measuring the pressure of a gas in the abdominal cavity; a first port for insufflating and evacuating the abdominal cavity; a second pressure sensor for measuring the pressure of a gas in the hollow organ; a second port for insufflating and evacuating the hollow organ; and an air supply apparatus connected to the second port for controlling the air supply and evacuation based on the output by the first and second pressure sensors.

BRIEF DESCRIPTION OF THE DRAWINGS

FIG. 12 is a diagram in which the puncture needle through the endoscope is inserted to the stomach wall, insufflation of the abdominal cavity.

FIG. 13 is a diagram showing the overtube pressing into the stomach.

FIG. 14 is a flowchart of the pressure regulation.

FIG. 15 is a diagram of the stomach wall being aspirated into the overtube.

FIG. 16 is a diagram showing the formation of an opening of the aspirated stomach wall by means of a high frequency knife.

FIG. 19 is a diagram of the stomach wall being aspirated into the overtube.

FIG. 20 is a diagram showing the formation of an opening of the aspirated stomach wall by means of a high frequency knife.

FIG. 23 is a diagram showing an embodiment in which there is an attached tube used for air exhaust on the outer side of the overtube.

FIG. 32A illustrates an isometric view of an overtube according to a first embodiment where the overtube is shown together with an endoscope, and the distal end of the endoscope is inserted through an incision in the stomach.

FIG. 32B illustrates a sectional view of the overtube and endoscope as taken along line A-A in FIG. 32. (The wall of the esophagus is not shown).

FIG. 33 illustrates an isometric view of an overtube according to a second embodiment, where the overtube is shown together with an endoscope, and the overtube and the endoscope are inserted through an incision in the stomach.

FIG. 34A illustrates an isometric view of an overtube according to a third embodiment, where the overtube is shown together with an endoscope, and the overtube and the endoscope are inserted through an incision in the stomach.

FIG. 34B illustrates a sectional view taken along line A-A in FIG. 34A.

DETAILED DESCRIPTION OF THE INVENTION

Figure 1:
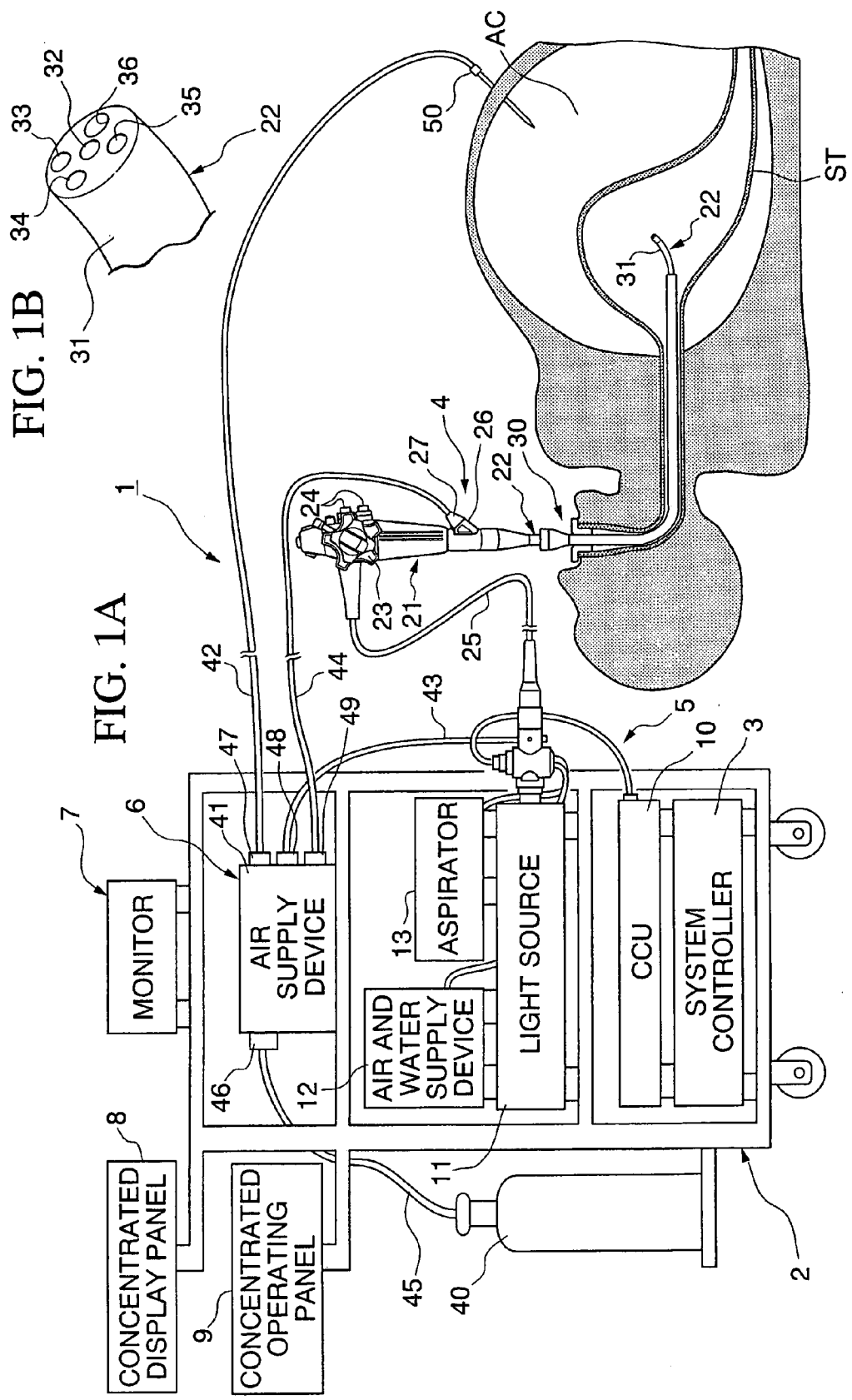
FIG. 1A is a diagram showing the entire structure of a medical system which includes an example of a device for accomplishing a medical operation.
FIG. 1B is a partially enlarged diagram of FIG. 1A.

Embodiments will be hereafter explained in detail. In the following description, the same reference symbols are used for the same components, and duplicate description is omitted.

First Embodiment

In FIG. 1A, a description is provided of the medical system used in the present embodiment. Medical system 1 includes a system controller 3 mounted on a cart 2, an endoscope system 5 which includes an endoscope 4 which is inserted into a body, an air supply system 6, a monitor 7 which is the display device, a collective panel 8, and a collective operating panel 9.

The system controller 3 entirely controls the medical system 1. Connected to the system controller 3 are a collective display panel 8, a collective operating panel 1, and an endoscope system 5 and the like so that through a two-way communication can be carried out via a communication line not shown in the drawings.

The endoscope system 5 accomplishes a medical operations to a hollow organ or the abdominal cavity from the mouth of the patient, and includes the flexible the endoscope 4, a camera control unit (hereinafter referred to as CCU) 10, a light source 11, an air and water supply device 12, and an aspirator 13.

The endoscope 4 includes an operating unit 21 operated by an operator, and a long flexible insertion device is extendably attached from the operating unit 21. The operating unit 21 is arranged with an angle knob 23 which bends the insertion device 22, and various buttons 24, connected to the system light source 11 by means of a universal cable 25. To the side of the operating unit 21 is attached a treatment tool insertion portion 26 for inserting the treatment tool, and to which a stopper 27 is tightly fitted. Moreover, in FIG. 1A, the endoscope 4 is inserted through the stomach ST through an overtube 30 which guides its insertion to within the body. However, the overtube is not necessarily required.

To the distal end of insertion unit 22 is attached a bendable end unit 31. As shown in FIG. 1B, on the distal end surface of the insertion unit 22 is arranged an observation device 32, an illumination device 33, an end opening of an air and water channel 34, an end opening of an aspiration channel 35, and an end opening of a the operation channel 36.

The observation device 32 includes an observation optical system and photographic image device, which converts an in vivo optical image to an electrical signal, and outputs it to the CCU 10 through the universal cable 25. The CCU 10 converts an electrical signal sent from the observation device 32 to a video signal, and displays the in vivo optical image on a monitor 7 or the collective display panel 8. The illumination device 33 includes an illumination window and light guide, which provides in vivo illumination with illumination light supplied from the light source 11.

Air and water are supplied to the air and water supply channel 34 from the air and water supply device 12 through the universal cable 25. The aspiration channel 35 is connected to the aspirator 13 through the universal cable 25. An operation channel 36 is connected to the treatment tool insertion portion 26 on the side of the operating unit 21 passing within insertion unit 22. However, the structure of the endoscope 4 is not limited to this. For example, in this configuration, the work channel 36 may be used for suction work instead of omitting the suction channel 35.

The monitor 7 receives a video signal output from the CCU 10, and the endoscope picture image is displayed. The display screen, e.g., a liquid crystal display is attached to the collective display panel 8. The collective display panel 9 has a display screen collectively displaying the image output by the endoscope and operation state of components output from the system controller. The concentrated operation panel 9 is configured susceptible of input associated with various operation and setup by means of a touch sensor. Each system can be remotely operated using the concentrated operation panel 9.

Primary structural components of the air supply system 6 are a gas cylinder 40 which is the supply source of the liquid used for insufflation, an air supply device 41, and the tubes 42, 43, and 44 which extend toward the patient from the air supply device 41. A gas cylinder 40 is filled with a liquefied high-pressure carbon dioxide gas. A high-pressure gas tube 45 extending from the gas cylinder 40 is coupled to a high-pressure metal cap 46 of the air supply device 6. Provided to the air supply device 41 in addition to the high-pressure metal cap 46 are an insufflation metal cap 47, a luminal metal cap 48, and a pressure measurement metal cap 49.

The tube 42 connected to the insufflation metal cap 47 is connected to an pneumoperitoneum needle 50. The tube 43 connected to the luminal metal cap 48 is connected to the air and water supply channel 34 through the universal cable 25 of the endoscope 4. The tube 44 connected to the pressure measurement metal cap 49 is inserted from stopper 27 of the endoscope 4, and is led to the distal end of the operating channel 36. The tubes 42-44 are formed from silicon resin or Teflon®.

Figure 2:
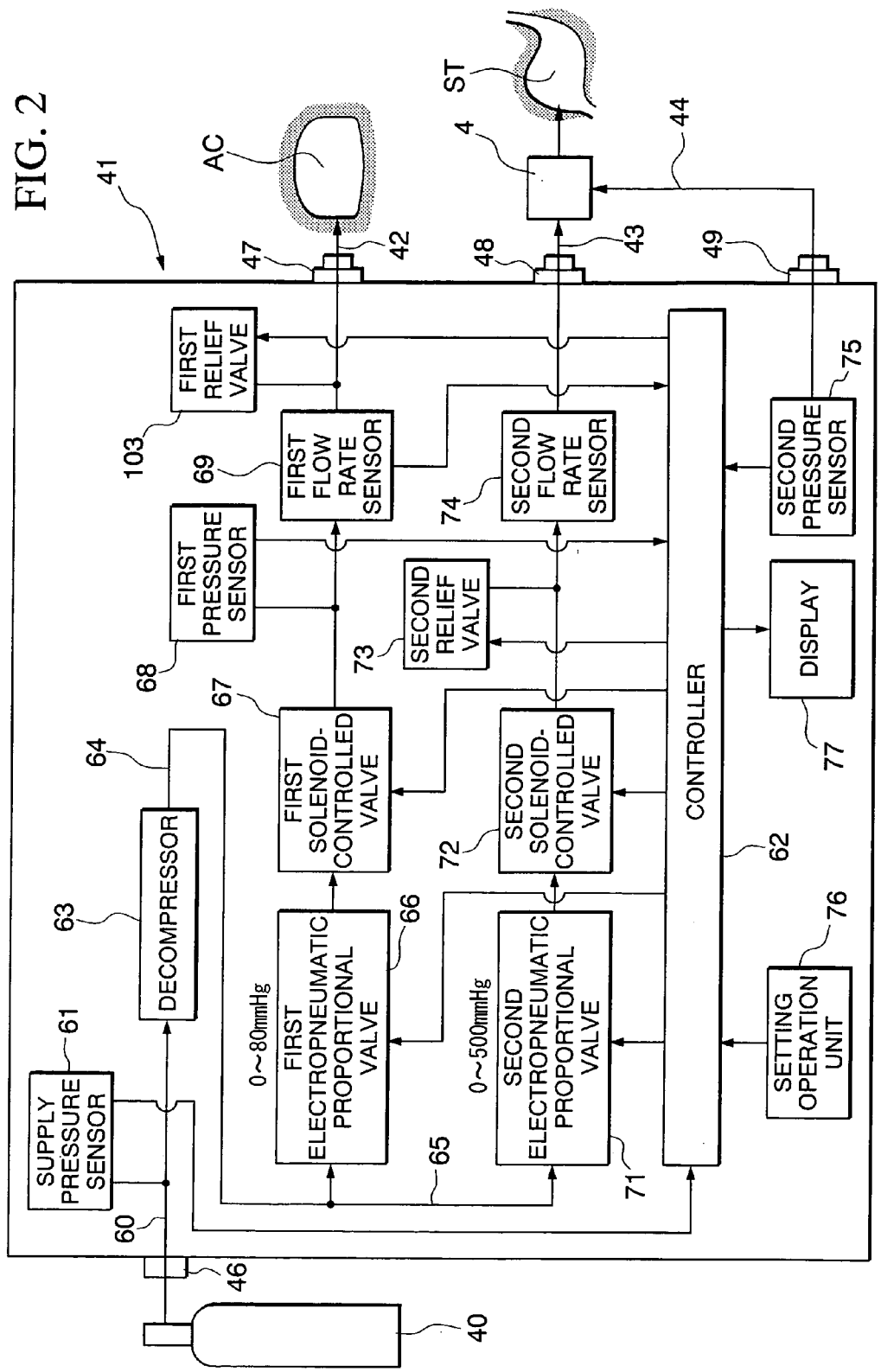
FIG. 2 is a diagram showing the structure an air supply device.

FIG. 2 shows the air supply device 41 in a schematic view.

A supply pressure sensor 61 attached to the flow path 60 connected to the high-pressure metal cap 46 in the air supply device 41 measures the pressure of carbon dioxide gas supplied from the gas cylinder 40 and outputs to the controller 62. A decompressor 63 is provided downstream relative to the supply pressure sensor 61. The decompressor 63 reduces the high-pressure gas to a specific pressure. A first flow path 64 directed toward the insufflation metal cap 47 is formed downstream of the decompressor 63 where a second flow path 65 separating from the first flow path 64, is extended toward the luminal metal cap 48.

Provided in the first flow path 64 in the order from the upstream are a first electropneumatic proportional valve 66, a first solenoid-controlled valve 67, a first pressure sensor 68, a first flow rate sensor 69, and a first relief valve 103. The first electropneumatic proportional valve 66 changes the force of the decompression spring operating on the valve based on a control signal from the controller 62, electrically regulating the pressure of carbon dioxide gas. The first electropneumatic proportional valve 66 regulates the air supply pressure of the carbon dioxide gas within a range between 0 to 80 mmHg. The first pressure sensor 68 measures the pressure value Pa within the abdominal cavity AC through the first flow path 64. The first flow rate sensor 69 measures the flow rate of carbon dioxide gas flowing through the first flow path 64, and outputs it to the controller 62. The first relief valve 103 is a solenoid-controlled valve which accomplishes an open/close operation by means of a signal from the controller 62.

Provided in the second flow path 65 in the order from the upstream are a second electropneumatic proportional valve 71, a second solenoid-controlled valve 72, a second relief valve 73, and a second flow rate sensor 74. The second electropneumatic proportional valve 71 regulates the air supply pressure of the carbon dioxide gas within a range between 0 to 500 mmHg by means of the control signal of the controller 62. The second relief valve 73 is a solenoid-controlled valve which accomplishes an open/close operation based on the control signal from the controller 62. The second flow rate sensor 74 measures the flow rate of carbon dioxide gas flowing through the second flow path 65, and outputs it to the controller 62.

Furthermore, to the pressure measurement metal cap 49 is attached a second pressure sensor 75. The second pressure sensor 75 measures the pressure value Ps in the stomach ST, and its output is input to the controller 62. Moreover, a setting operation unit 76 and a display 77 are also connected to the controller 62. The setting operation unit 76 and the display 77 receive a particular display or operation related to the air supply device 41, and are provided, for example, on the front surface panel of the air supply device 41. As the setting operation unit 76, an electric power switch, an air supply start button, or an air supply suspension button may be used. The display 77 may be a residual gas amount display displays the result of output obtained by the supply pressure sensor 61.

A medical operation using the medical system 1 illustrated in FIG. 1 will be explained next.

Described hereunder is a procedure for treating an organ or a tissue (hereunder, called a target site) by means of the endoscope 4 inserted through natural orifice of an organ, e.g., a mouth of a patient. However, the natural orifice subject to the insertion of the endoscope 4 is not limited to the mouth, and may be a nostril or an anus. Moreover, treatments as a medical operation are applicable to various actions such as suture, observation, incision, and cell sampling.

The insertion unit 22 of the endoscope 4 is inserted from the mouth of the patient, and the distal end of the insertion unit 22 is introduced into the stomach ST. In addition, the pneumoperitoneum needle 50 is inserted into the abdominal cavity AC through the abdominal wall of the patient.

Initially, air is delivered into the stomach ST through a tube 43 from the air supply device 41, inflating the stomach ST so that visual inspection of an incision target site can be obtained by means of the endoscope 4. At this time, an operator operates a condensed operation panel 9 or the air supply device 41 shown in FIG. 1 to select the second pipe channel 65, and sets the pressure in the stomach ST. The controller 62 shown in FIG. 2 actuates the second electropneumatic proportional valve 71, thereby opening the second solenoid-controlled valve 72. The controller 62 sets the degree of opening of the second electropneumatic proportional valve 71 based on the output by a second flow rate sensor 74. The carbon dioxide gas within the air cylinder 40 is delivered to the air and water supply channel 34 in the endoscope 4 through the tube 43 from the second of flow path 65, further to the inside of the stomach ST from the distal end opening. Inflow of carbon dioxide gas increases the pressure in the stomach ST.

The pressure value Ps of the stomach ST obtained through the tube inserted into the operating channel 36 is measured by the second pressure sensor 75. The controller 62 compares the pressure value Ps (actually measured value) of the second pressure sensor 75 with the target pressure set by the operator. If the pressure value Ps does not reach the target pressure, degree of opening of the second electropneumatic proportional valve 71 is adjusted according to the difference between the target pressure and the pressure value Ps, thereby changing the air supply pressure. On the other hand, if the pressure value Ps is greater than the target pressure, the second solenoid-controlled valve 72 is closed, stopping the supply of carbon dioxide gas to the stomach ST, and atmospheric release is accomplished by opening the second relief valve 73, if necessary. In this manner, the air supply device 41 controls to maintain the air in the stomach ST at a specific pressure.

Used for confirming the incision on the stomach ST is the observation device 32 of the endoscope 4. At this time, a high frequency treatment tool or a clip or the like, may also be used for providing a mark to the target position of the body to be incised.

Care must be taken not to hurt organs around the gastric wall while insufflating the abdominal cavity by means of air by driving the air supply system 6. At this time, the operator manipulating the concentrated operation panel 9 or air supply unit 41 selects the air supply to the tube 42. Furthermore, the operator sets the pressure within the abdominal cavity AC. The controller 62 shown in FIG. 2 actuates the first electropneumatic proportional valve 66, thereby opening a first solenoid-controlled valve 67. The degree of opening of the first electropneumatic proportional valve 66 is set by the controller 62 based on the output of the first pressure sensor 68 and the first flow rate sensor. Carbon dioxide gas in the compressed gas cylinder 40 is sent from the first flow path 64 to the abdominal cavity through the pneumoperitoneum needle 50 and the tube 42. The inflow of the carbon dioxide gas increases the pressure in the abdominal cavity AC. The pressure value Pa of the abdominal cavity AC can be measured by the first pressure sensor 68. The controller 62 closes the first solenoid-controlled valve 67 to measure the pressure in the abdominal cavity AC. Since the supply of carbon dioxide gas from the air cylinder 40 is suspended, the measurement value obtained by the first pressure sensor 68 after the lapse of a predetermined time period becomes the pressure value Pa in the abdominal cavity AC.

The controller 62 compares the pressure value Pa (actual measured value) of the abdominal cavity AC measured by the first pressure sensor 68 with a target pressure set by the operator. If the pressure value Pa does not reach the target pressure, the degree of opening of the first electropneumatic proportional valve 66 is adjusted based on the difference between the target pressure and the pressure value Pa, thereby changing the air supply pressure. On the other hand, if the pressure value Pa is greater than the target pressure, the first solenoid-controlled valve 67 is closed, and the supply of carbon dioxide gas to the abdominal cavity AC is suspended. Subsequently, opening the first relief valve 103 to release it to the atmospheric pressure decreases the pressure value Pa in the abdominal cavity AC. This is how the air supply device 41 controls to maintain the pressure in the abdominal cavity AC at a specified pressure.

Moreover, if the abdominal cavity AC has been previously insufflated, pressure in the stomach ST may be regulated greater than that in the pressure in the abdominal cavity AC.

Figure 3:
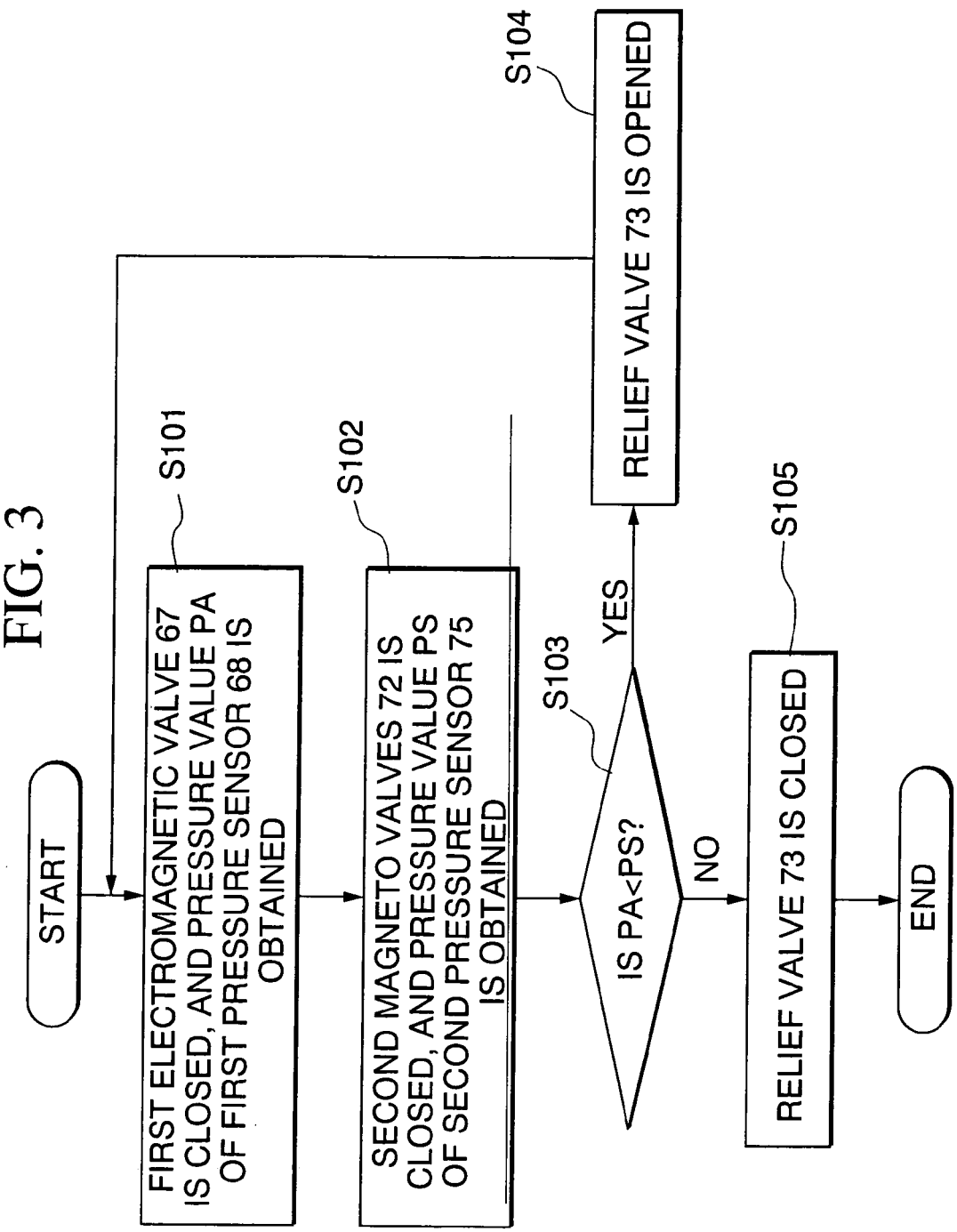
FIG. 3 is a flowchart of the pressure regulation.

Once the target site for incising the body has been confirmed, the air in the stomach ST is exhausted by the air supply device 41 and the pressure value Ps in the stomach ST is reduced to the pressure value Pa of the abdominal cavity AC or less. As shown in FIG. 3, the first solenoid-controlled valve 67 is closed, and the pressure value Pa of the first pressure sensor 68 is obtained (step S101). Next, the second solenoid-controlled valves 72 are closed, and the pressure value Ps of the second pressure sensor 75 is obtained (step S102). The controller 62 compares the values of the pressure values Pa and Ps, and if the pressure value Ps in the stomach ST is greater than the pressure value Pa of the abdominal cavity (YES in step S103), then a second relief valve 73 is opened (in step S104). Since the second relief valve 73 is provided to the second flow path 65 of the air supply device 41, carbon dioxide gas in the stomach ST is exhausted to the outside of the body through the air and water supply channel 34. Subsequently, the process returns to the step S101, and the steps S101 to S104 are repeated until the pressure value Ps in the stomach ST reaches the pressure value Pa of the abdominal cavity AC or lower. Since the second relief valve 73 is in the open state during that period, the pressure in the stomach ST is gradually reduced. If the pressure value Ps in the stomach ST is reduced to the pressure value Pa of the abdominal cavity AC or lower (No in step S103), the second relief valve 73 is closed (in step S105), and the process thereof is terminated. Moreover, the procedure may proceed to step S105 when the pressure value Ps in the stomach ST becomes lower by a specific difference than the pressure Pa.

After adjusting the pressure of the stomach ST, a treatment tool used for making incision, e.g., a high frequency knife, is passed through operation channel 36 of the endoscope 4, and the stomach wall is incised. The incision can be conducted directly by a knife of a high-frequency type.

Figure 4:
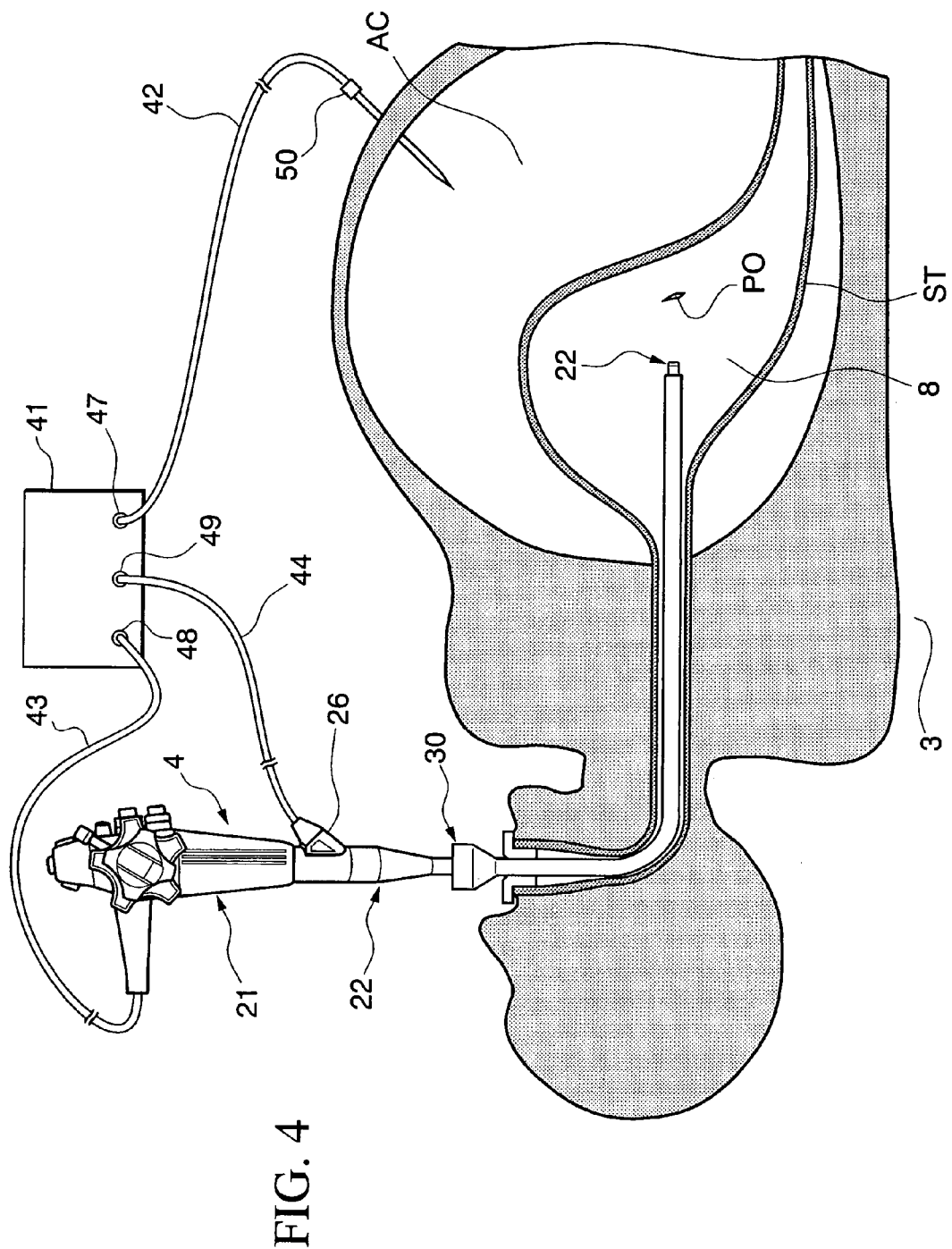
FIG. 4 is a diagram illustrating a medical operation, and a diagram which forms an opening in the stomach.

As shown in FIG. 4, an opening PO is formed in the stomach wall. However, since the pressure value Ps in the stomach ST is equal to or less than the pressure value Pa within the abdominal cavity AC, outflow of carbon dioxide gas or any other fluid (hereinafter referred to as a fluid) from the stomach ST to the abdominal cavity AC can be prevented, keeping the abdominal cavity AC clean, and preventing infection, from the viewpoint of using pressure control in the stomach ST and the abdominal cavity AC.

The insertion unit 22 is advanced, and the abdominal cavity AC is accessed by passing the endoscope 4 and the overtube 30 through the opening PO made by incising the stomach wall. At this time, carbon dioxide gas delivered through the first flow path 64 of the air supply device 41 insufflates the abdominal cavity. While performing medical operations within the abdominal cavity AC, the second solenoid-controlled valve 72 is maintained in its closed state, and no air is delivered through the second flow path 65. Another insulation is conducted in this step because a space for performing the medical operation must be provided within the abdominal cavity AC.

Figure 5:
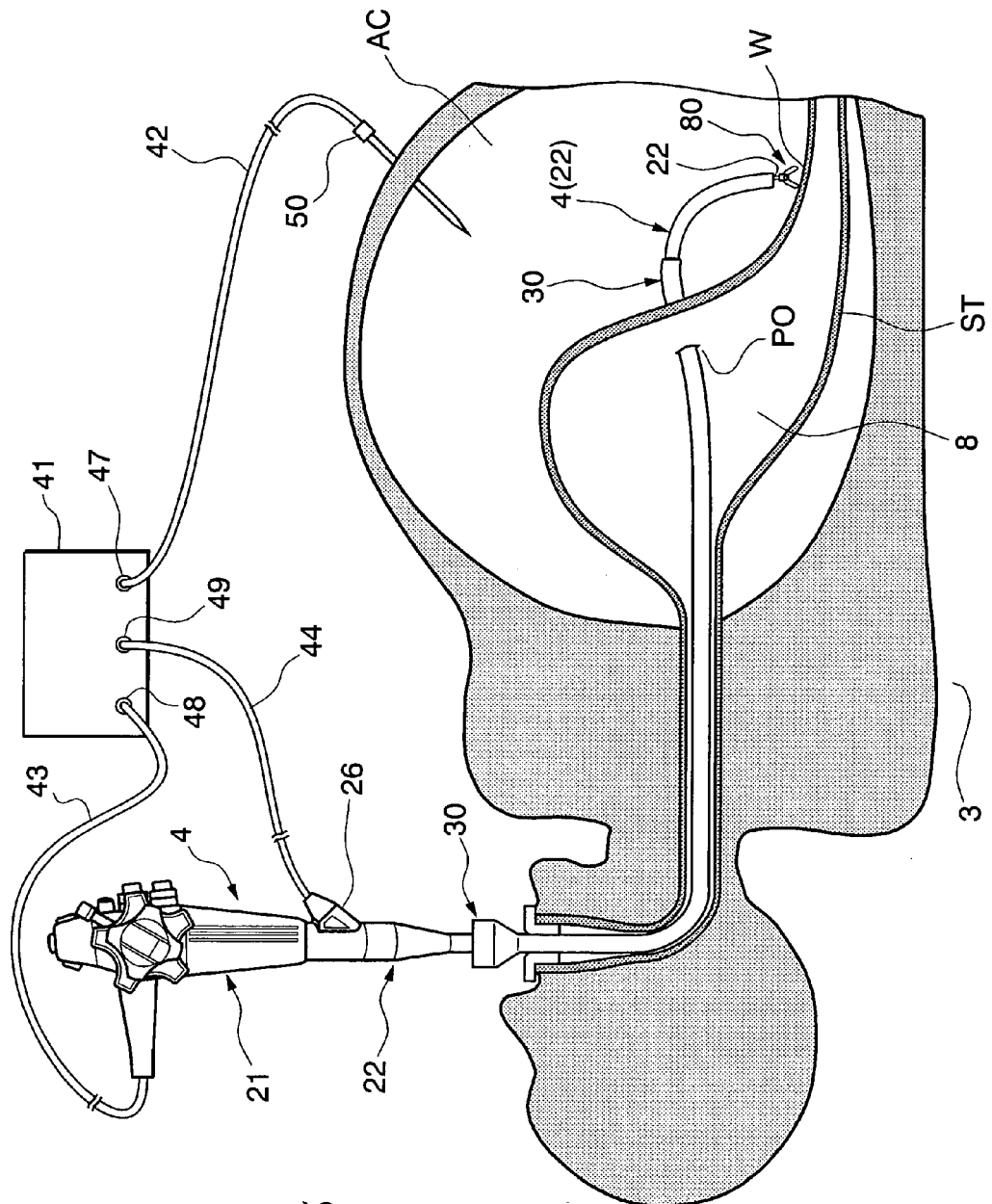
FIG. 5 is a diagram which shows one mode of performing a medical operation in which an endoscope is introduced to the abdominal cavity through an opening in the stomach.
Figure 6:
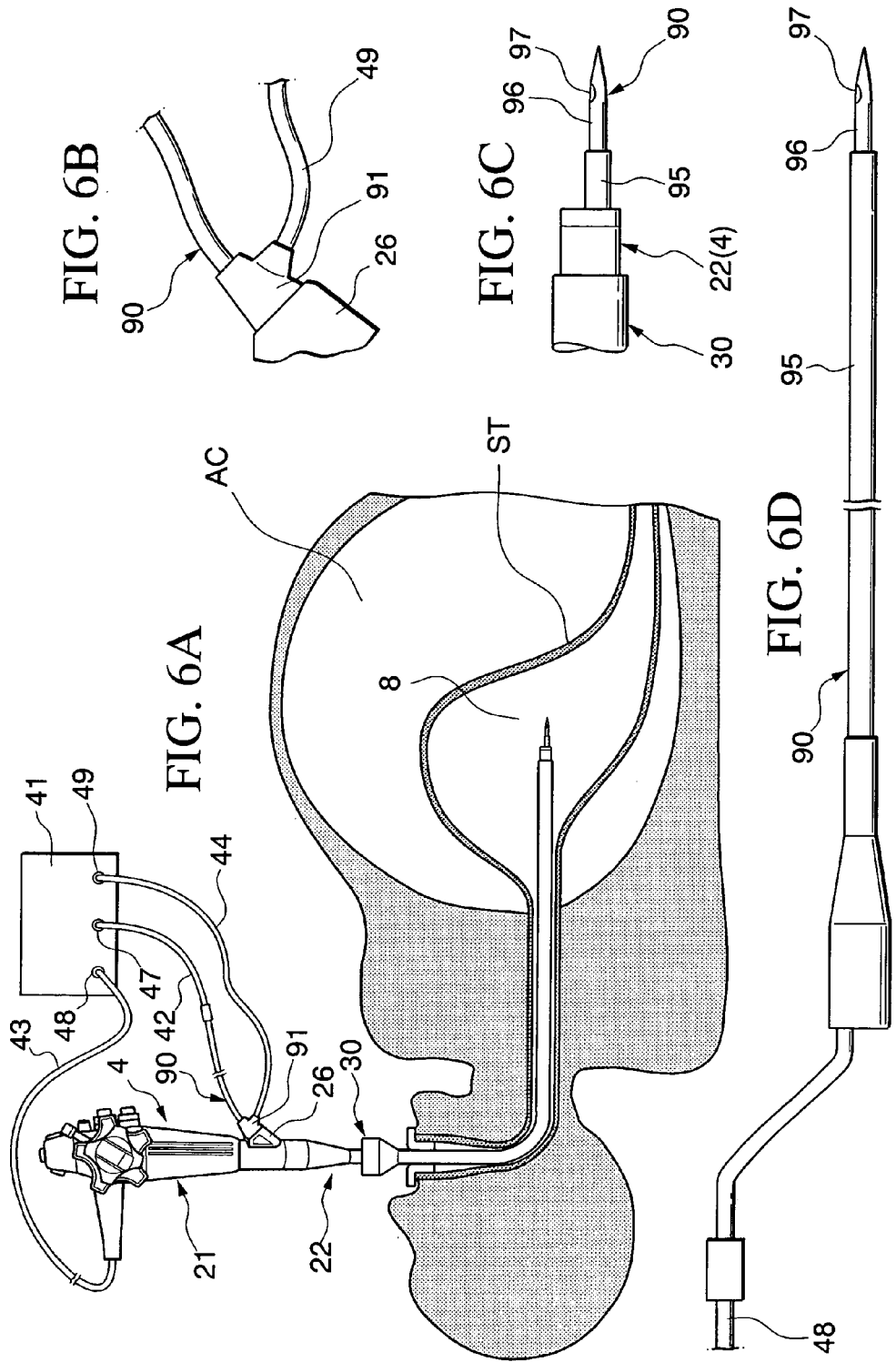
FIG. 6A is a diagram illustrating the air supply route according to another embodiment.
FIG. 6B is an enlarged diagram of the stopper shown in FIG. 6A.
FIG. 6C is an enlarged diagram of the distal end of the endoscope shown in FIG. 6A.
FIG. 6D is an enlarged diagram of a puncture needle.

As shown in FIG. 5, the endoscope 4 is advanced in the insufflated abdominal cavity AC, and the distal end surface of the endoscope 4 is faced toward the target site W. While observing the target site W with the observation device 32, treatment is conducted using the treatment tool 80 passing through the operating channel 36. For example, forceps passing through the operating channel can be used to remove a tissue. In addition, a high frequency treatment tool passing through the operating channel 36 can burn the target site W.

Preferably, smoke produced at the time of burning is discharged to the outside of the body through the aspiration channel 35 or the air supply device 41 so as to ensure the clear field of view of the endoscope 4.

Upon completion of the medical operation, the endoscope 4 and the overtube 30 are withdrawn to the stomach ST. Since no carbon dioxide gas is supplied to the stomach ST since cutting the stomach wall until the completion of the medical operation, the pressure value Ps in the stomach ST is equal to or less than the pressure value Pa of the abdominal cavity AC. Furthermore, since the opening PO of the stomach ST is pressed and broadened by the overtube 30, the opening PO is spontaneously closed by removing the overtube 30. Accordingly, even if the endoscope 4 and the overtube 30 are withdrawn to the stomach ST, there is no outflow of fluid from the stomach ST to the abdominal cavity AC.

At this instance, the operator may confirm that the pressure value Ps in the stomach ST is equal to or less than the pressure value Pa of the abdominal cavity AC prior to withdrawing the endoscope 4 and the overtube 32 to in the stomach ST. In this case, in order to detect the pressure value in the stomach ST, a separate pipe channel is inserted into the stomach ST from the mouth (natural orifice) of the patient, and the pressure value Ps is confirmed by viewing a pressure gauge connected to the pipe channel. This reliably prevents the outflow of the fluid from the stomach ST to the abdominal cavity AC. Moreover, if the pressure value Ps in the stomach ST is equal to or less than the pressure value Pa of the abdominal cavity AC, the pressure in the stomach ST is reduced in accordance with the flow shown in FIG. 3.

Subsequently, the opening PO is sutured from the inside of the stomach ST using a suture instruments passing through the operating channel of the endoscope 4 which has been returned to the stomach ST. A leak test may be carried out in order to confirm that the opening PO has been completely sutured. In the leak test, water is supplied to the sutured portion of the stomach ST from the air and water supply channel 34 of the endoscope 4. If the suture is incomplete, bubbles are produced in the stomach ST. If no bubbles are produced, the water in the stomach ST will be absorbed through the aspiration channel 35 of the endoscope 4. After suspending the supply of carbon dioxide gas to the abdominal cavity AC, the tube 42 is removed from the pneumoperitoneum needle 50, and the gas is discharged into the atmosphere from the abdominal cavity AC. In addition, the controller 62 opens the second relief valve 73 to discharge carbon dioxide gas of the stomach ST, thereby returning the stomach ST to atmospheric pressure. Subsequently, the pneumoperitoneum needle 50 is removed from the abdominal wall, and the endoscope 4 and the overtube 30 are removed from the patient's mouth.

As explained above, the pressure of the abdominal cavity AC is controlled during the medical operation using the endoscope inserted from the mouth of the patient so that the pressure value Ps in the stomach ST should be equal to or less than the pressure value Pa of the abdominal cavity AC prior to making an incision in the stomach ST. The pressure in the stomach ST must be higher than the pressure within the abdominal cavity AC in ordinary cases where an opening of the stomach wall of a target site must be confirmed. In such cases, releasing as desired the pressure in the stomach ST can prevent an outflow of fluid from the stomach S to the abdominal cavity AC when the stomach ST is incised, thereby maintaining the abdominal cavity clean and preventing infection.

In addition, in the present embodiment, an outflow of fluid from the stomach ST to the abdominal cavity AC can be prevented when the endoscope 4 and the overtube 30 are withdrawn from the abdominal cavity AC to the stomach ST after the completion of a medical operation, since the pressure value Ps in the stomach ST is equal to or less than the pressure Pa of the abdominal cavity AC during the period in which a medical operation is performed in the abdominal cavity AC. The abdominal cavity AC can be maintained clean similarly to the inserted state, thereby preventing infection.

Second Embodiment

As shown in FIG. 6A to FIG. 6D, the luminal metal cap 48 of the air supply device 41 is connected to the air and water supply channel 34 of the endoscope 4 through the tube 43. The insufflation metal cap 47 is connected to a lumen of the treatment tool, e.g., a puncture needle 90 through the tube 42. The puncture needle 90 is passed through the operating channel 36 via a stopper 91 attached to the treatment tool insertion portion 26 of the endoscope 4. The stopper 91 has two branches. A pressure-measuring tube 44 is inserted into an opening of one of the branched portions.

The puncture needle 90 has a needle member 96 that can freely extend and retract in a protective sheath 95. A lumen is formed within the needle member 96. The proximal end of the lumen is connected to a tube 42. An opening 97 is formed in the vicinity of a sharp tip of a needle member 96 on the distal end of the lumen.

A medical operation in the present embodiment will be explained. The present embodiment differs from the first embodiment only with respect to a route for supplying carbon dioxide gas at the time of insufflation.

The puncture needle 90 is inserted through the operating channel 36 of the endoscope 4, connected to the air supply device 41, and further inserted into the patient's stomach ST.

Carbon dioxide gas is supplied next to the air and water supply channel 34 to inflate the stomach ST. The pressure value Ps in the stomach ST is measured by a second pressure sensor 75 of the air supply device 41 through the tube 44 inserted into the two-way stopper 91.

Figure 7:
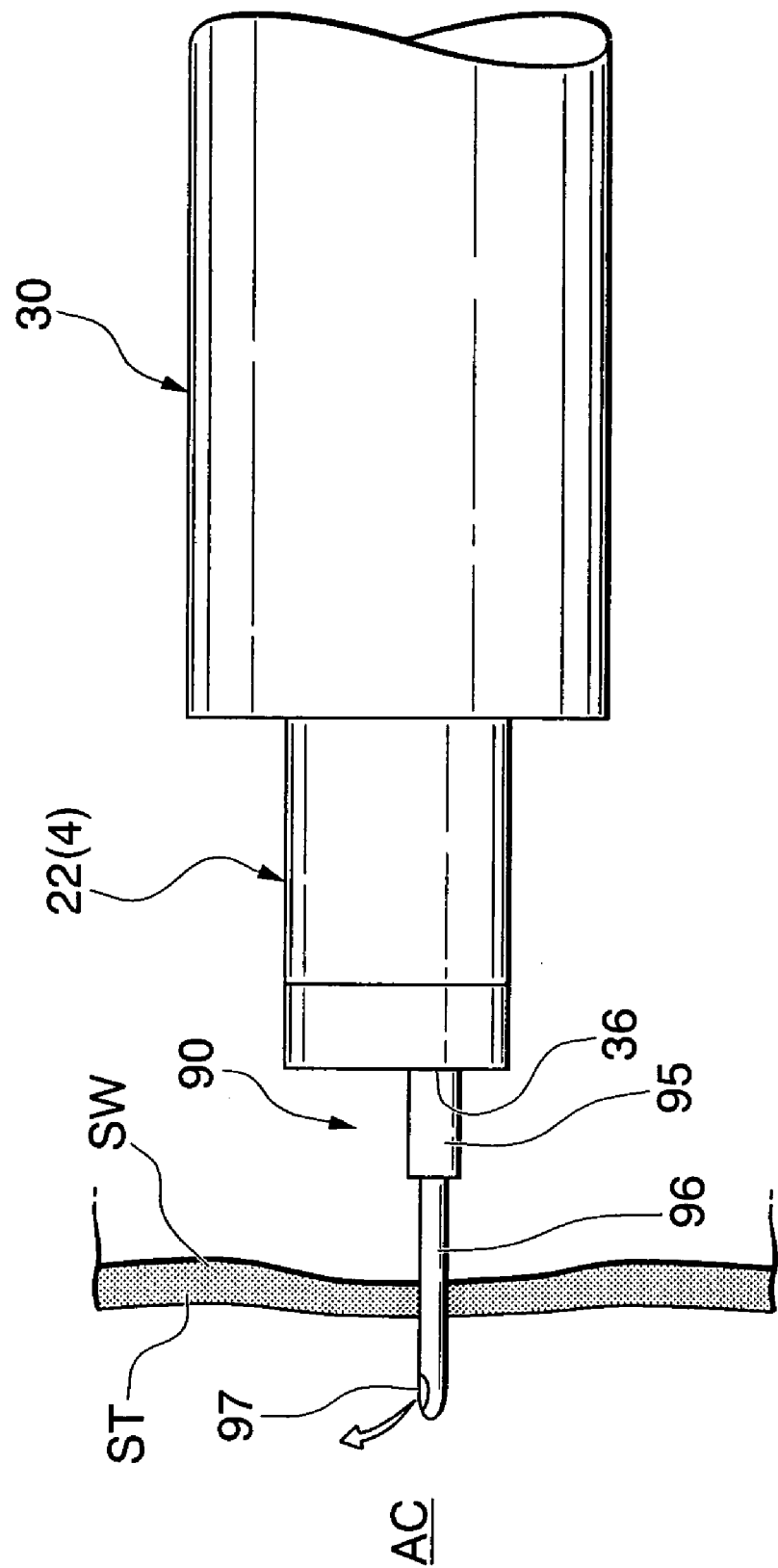
FIG. 7 is a diagram in which the puncture needle through the endoscope is inserted to the stomach wall, insufflation of the abdominal cavity.

As shown in FIG. 7, advancing the needle member 96 of the puncture needle 90 penetrates the stomach wall SW. At this time, the puncture needle 90 is pressed into the stomach wall SW until the distal end opening 97 of the lumen is exposed to the abdominal cavity AC.

The abdominal cavity AC is insulated by carbon dioxide gas supplied from the first flow path 64 of the air supply device 41. The carbon dioxide gas is provided to the abdominal cavity AC through the lumen within the puncture needle 90. The pressure value Pa of the abdominal cavity AC is measured by the first pressure sensor 68 (see FIG. 2).

The pressure value Ps in the stomach ST is set higher than the pressure value Pa of the abdominal cavity AC when the target site for cutting the stomach ST is confirmed.

The second relief valve 73 (see FIG. 2) of the air supply device 41 is released to the atmospheric pressure to control the pressure in the stomach ST When the stomach wall SW is incised. If the pressure value Ps in the stomach ST is equal to or less than the pressure value Pa of the abdominal cavity AC, an opening PO is formed by incising the stomach wall SW. The puncture needle 90 is withdrawn from the stomach wall SW when inserting the endoscope 4 into the abdominal cavity AC through the opening PO. After incising the stomach wall SW and inserting endoscope 4 and the overtube 30 therethrough, the insertion unit 22 is advanced to access the abdominal cavity AC. Accordingly, carbon dioxide gas supplied from the air supply device 41 through the second flow path 65 insufflates the abdominal cavity AC, thereby a medical operation is executed, during which the first solenoid-controlled valve 67 remains in the closed state. The procedures thereafter are the same as those of the first embodiment.

In the present embodiment, the controlled pressure in the stomach ST and abdominal cavity AC prevents the outflow of fluid from the stomach ST to the abdominal cavity AC, thereby continuously maintaining the clean state and preventing infection. Furthermore, since there is no need for implanting the pneumoperitoneum needle 50 in the abdominal wall, the medical operations can be conducted without causing an injury to the patient.

Third Embodiment

Figure 8:
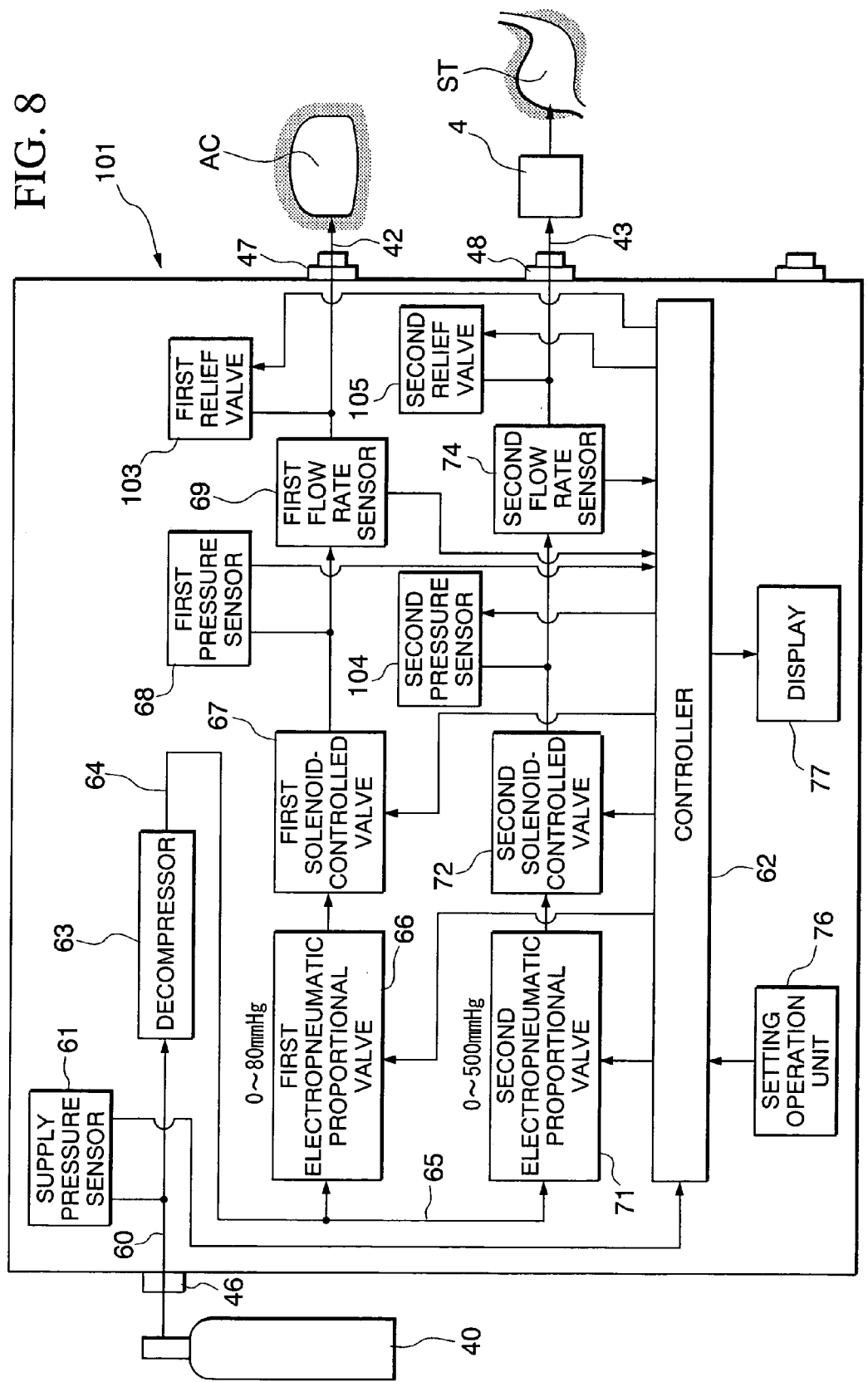
FIG. 8 is a diagram showing the structure an air supply device.

FIG. 8 shows the structure of the air supply device used in the present embodiment.

An air supply device 101 has a second pressure sensor 104, the second flow rate sensor 74, and a second relief valve 105 in this order is connected to the second solenoid-controlled valve 72 on the second flow path 65 branching from the decompressor 63. The air supply device 101 is connected to the tube 43. The first and second relief valves 103 and 105 respectively are solenoid-controlled valves capable of being atmospherically released by the control signal of the controller 62.

Figure 9:
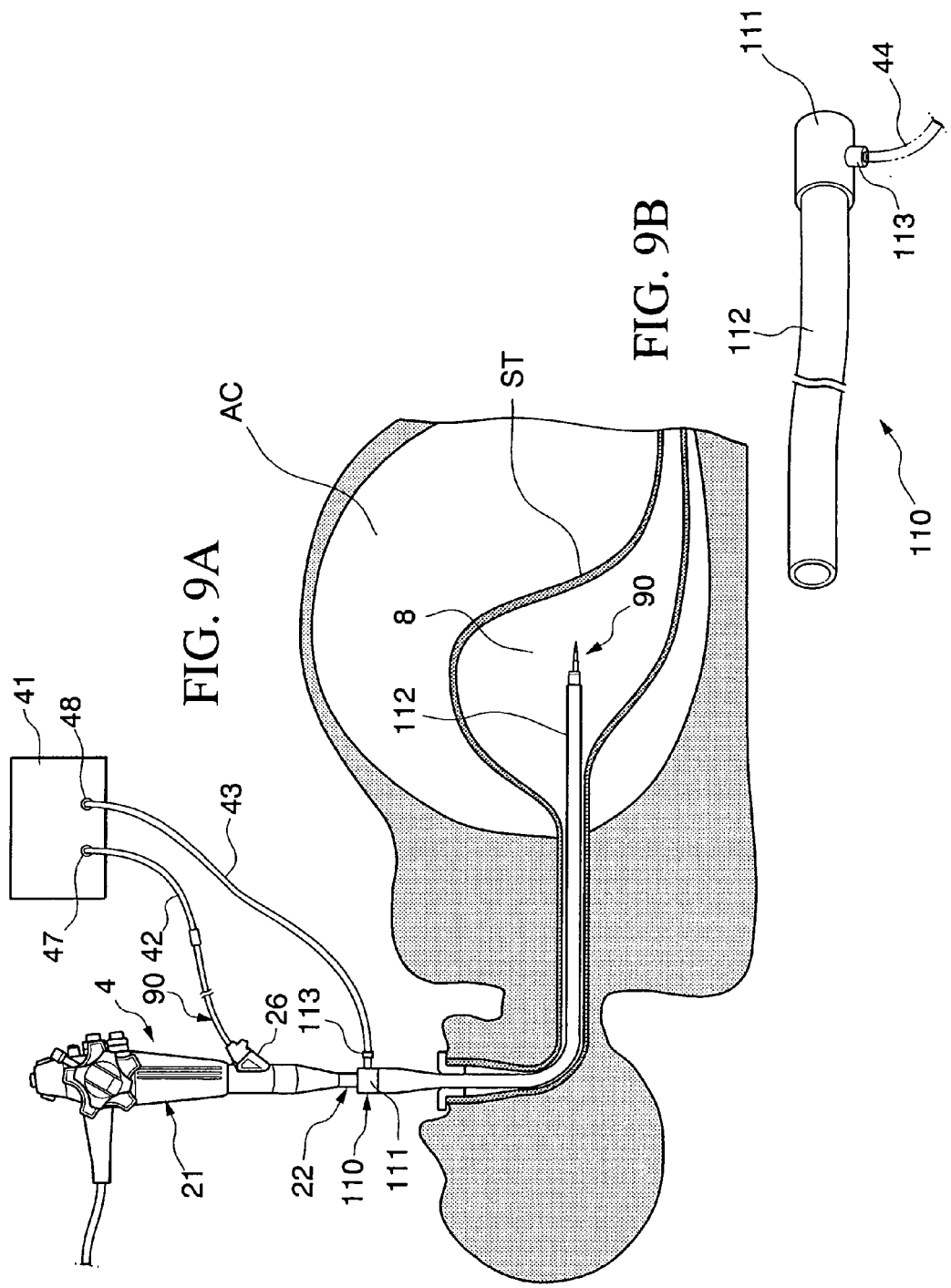
FIG. 9A is a diagram illustrating the air supply route according to another embodiment.
FIG. 9B is an enlarged diagram of the overtube shown in FIG. 9A.

As shown in FIG. 9A, the tube 42 extending from the insufflation metal cap 47 of the air supply device 101 is connected to the lumen of the puncture needle 90. The tube 43 extending from the luminal metal cap 48 is connected to an overtube 110. As shown in FIG. 9B, a long flexible pipe 112 extends from the proximal end 111 of the overtube 110. Secured in the inner flange circumference of the proximal end 111 into which the endoscope 4 is inserted is an air tight valve (not shown in the drawing) forming air tight construction between the endoscope 4 and the overtube 110. Provided protrudingly toward the distal end from the air tight valve is a port 113 to which the tube 44 is connected. A hole which communicates with the overtube 110 is formed in the port 113.

Figure 10:
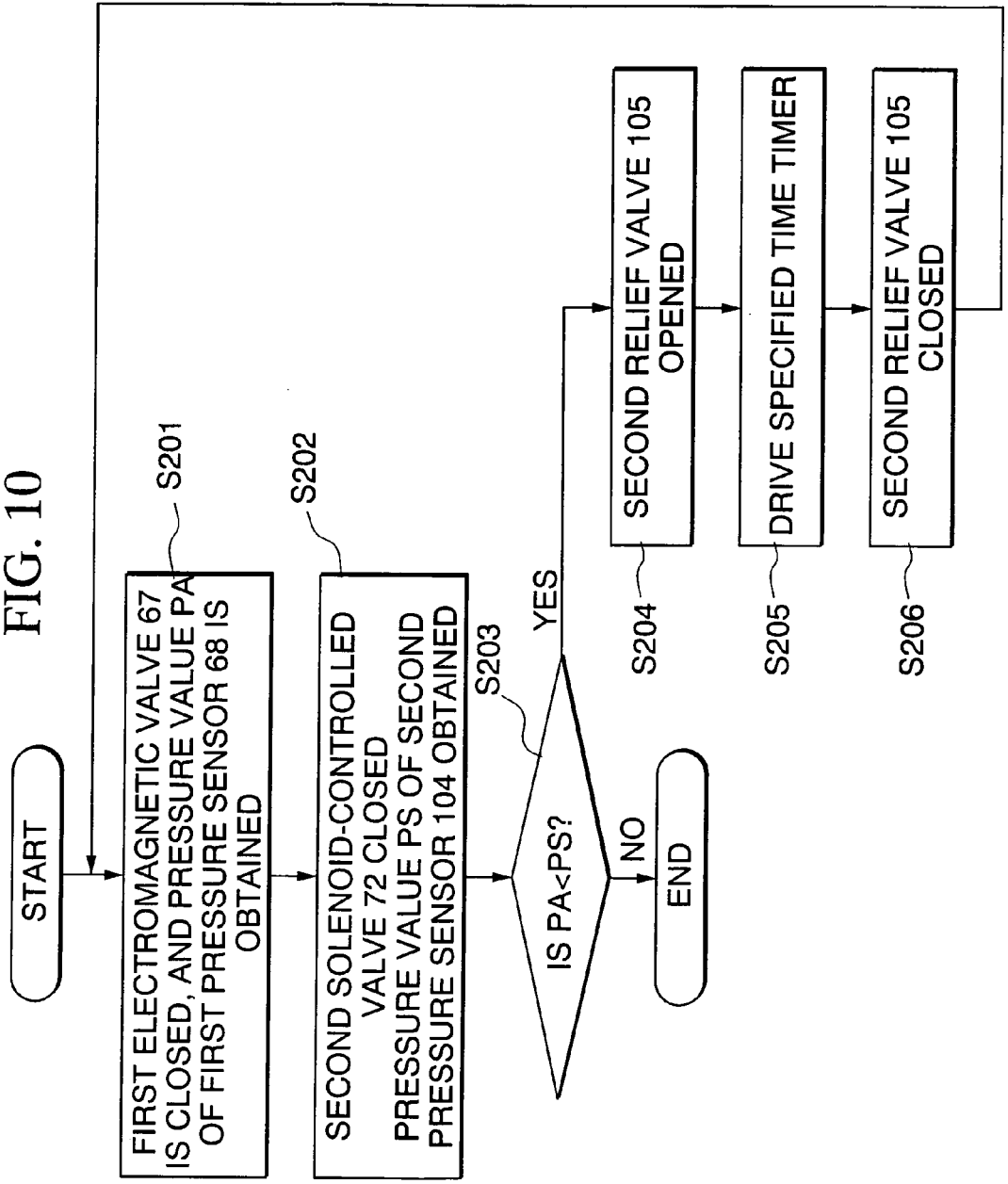
FIG. 10 is a flowchart of the pressure regulation.

When performing a medical operation, insufflating the stomach ST by supplying carbon dioxide gas through the overtube 110, thereby inflating the stomach ST and further insufflating the abdominal cavity AC with a puncture needle 90. The pressure control is conducted in accordance with the flow shown in FIG. 10 in order to incise the stomach wall while the pressure value Ps in the stomach ST is higher than the pressure value Pa of the abdominal cavity AC.

Initially, the first solenoid-controlled valve 67 is closed, and the pressure value Pa of the first pressure sensor 68 is obtained (in step S201) after a predetermined lapse of time period. Furthermore, the second solenoid-controlled valve 72 is closed, and the pressure value Ps of the second pressure sensor 104 is obtained (in step S202) after a predetermined lapse of time period. The controller 62 compares the pressure values Pa and Ps, and if the pressure value Ps in the stomach ST is greater than the pressure value Pa of the abdominal cavity AC (Yes in step S203), the second relief valve 105 is opened (in step S204). Since the second relief valve 105 is provided to the second flow path 65 of the air supply device 101, carbon dioxide gas in the stomach ST is exhausted to the outside of the body through the air and water supply channel 34. After the second relief valve 105 is opened, the timer of the controller 62 starts and the controller 62 stands-by (in step S205) until a predetermined time is reached. After a predetermined lapse of time, the second relief valve 105 is closed (in step S206), and the flow returns to step S201. Thereafter, steps S201 to S202 are repeated until the pressure value Ps in the stomach ST drops to the pressure value Pa of the abdominal cavity AC or less.

Since the second relief valve 105 is in the second flow path 65, it is difficult to accurately detect the pressure in the stomach ST with the second pressure sensor 104 while the second relief valve is in the open state; therefore, the release of the second relief valve 105 occurs only for the predetermined time. Also, if the pressure value Ps in the stomach ST is equal to or less than the pressure value Pa of the abdominal cavity AC (in step S203), processing of this flow is terminated. Moreover, the process may be terminated when the pressure value Ps in the stomach ST reaches a value which is lower than the pressure value Pa by a specified amount.

If the pressure value Ps in the stomach ST is equal to or less than the pressure value Pa within the abdominal cavity AC, the stomach wall is incised, and the endoscope 4 and overtube 110 are advanced to access the abdominal cavity AC. Subsequent medical operations are the same as those of the second embodiment.

In the present embodiment, independent pressure adjustment can be conducted since the pressure sensor 68 and the relief valves 103 are provided in the flow path 64 directed to the abdominal cavity AC, and the pressure sensor 104 and the relief valves 105 are provided in the flow path 65 directed to stomach ST. Also, the second pressure sensor 104 provided in the second flow path 65 eliminates necessity to arrange another pressure-measuring tube, thereby facilitating piping arrangement. Other effects are the same as those in the second embodiment.

Fourth Embodiment

Figure 11:
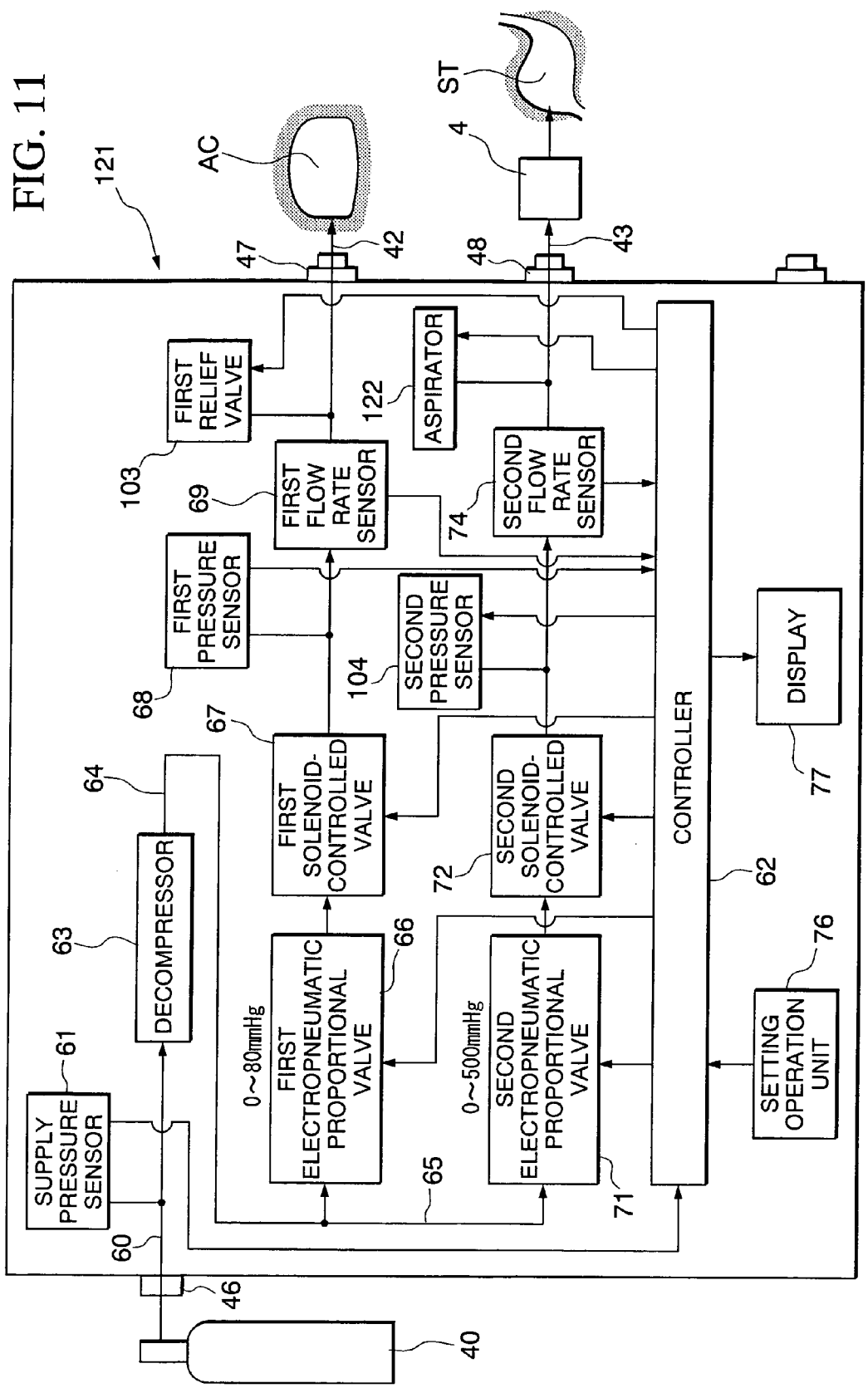
FIG. 11 is a diagram showing the structure an air supply device.

FIG. 11 shows the structure of the air supply device used in the present embodiment.

An air supply device 121 is connected to an aspirator 122 in the second flow path in lieu of the second relief valve. The connection among the air supply device 121, the endoscope 4, and overtube 110 is the same as that in the third embodiment.

An explanation is provided of the medical operation and the system of medical treatment. As shown in FIG. 12, after the insertion unit 22 of the endoscope 4 is inserted through the stomach ST, the stomach wall SW is penetrated by the puncture needle 90. The abdominal cavity AC is insufflated by supplying carbon dioxide gas through the puncture needle 90. Next, carbon dioxide gas is supplied from the overtube 110 to inflate the stomach ST until the pressure in the stomach ST is higher than the pressure within the abdominal cavity AC. The overtube 110 is advanced while the endoscope 4 is fixed after confirming the position subject to an incision. As shown in FIG. 13, the distal end portion of the overtube 110 is abutted to the stomach wall SW, including the position of the incision.

Conducted next prior to incising the stomach wall SW is to control the pressure in the stomach ST. As shown in the FIG. 14, the first solenoid-controlled valve 67 is closed, and after a predetermined lapse of time, the pressure Pa of the first pressure sensor 68 is obtained (in step S301). Further, the second solenoid-controlled valve 72 is closed, and after the lapse of a predetermined time period, the pressure value Ps of the second pressure sensor 104 is obtained (in step S302). If the pressure value Ps is higher than the pressure value Pa (Yes in step S303), the aspirator 122 is actuated. Since the second solenoid-controlled valve 72 is closed, carbon dioxide gas within the overtube 110 is absorbed. Simultaneously, the timer starts and the controller 62 stands-by (in step S304) until a predetermined time is reached, and then the aspirator 122 is terminated (in Step S305). Subsequently, the flow returns to step S301. The processes up to this point are repeated, and the process is terminated when the pressure value Ps becomes equal to or less than the pressure value Pa (No in step 303). Moreover, the process may be terminated when the pressure value Ps in the stomach ST reaches a value which is lower than the pressure value Pa by a specified amount.

The pressure lowered by the aspirator 122 in the space partitioned by the overtube 110 and the stomach wall SW becomes relatively lower than that of the periphery. As a result, as shown in FIG. 15, the stomach wall SW including the target incision position is drawn to the space 123 formed at the distal end of the overtube 110. The puncture needle 90 is removed from the operating channel 36, and is replaced by a high-frequency knife. As shown in FIG. 16, an opening is formed by incising the target open position with the distal end 131 of the high-frequency knife 130. During this time, since the pressure within the overtube 110 is maintained to be relatively low, even if the opening PO is formed in the stomach wall SW, there is no outflow of fluid from the overtube 110 to the abdominal cavity. The necessary medical operation is executed after advancing the endoscope 4 and the overtube 110 through the opening PO to access the abdominal cavity AC. Insufflation necessary during this period is executed by using the overtube 110. Upon the completion of a medical operation, the endoscope 4 is returned to the stomach ST, i.e., the inside of the overtube 110. Since air is not delivered to the entire stomach ST, the pressure value Ps in the stomach ST is equal to or less than the pressure value Pa of the abdominal cavity AC, and there is no outflow of fluid from the stomach ST to the abdominal cavity AC.

The time required to adjust the pressure can be shortened in the present embodiment since aspiration is accomplished by the aspirator 122 in lieu of accomplishing atmospheric release of the entire stomach ST for reducing the pressure value Ps. Furthermore, since the absorption conducted by the aspirator 122 absorbs the stomach wall SW including the target incision position into the overtube 110 provides a distance between the outside of the stomach wall SW and the other organs or abdominal wall. Owing to this, the stomach wall SW can be incised without affecting the other organs. Other effects are the same as indicated above.

Moreover, the stomach may be inflated, and marking may be provided to the target incision position by means a high-frequency treatment tool or a detainment tool, such as a clip. Furthermore, after providing the marking and absorbing the carbon dioxide gas having been supplied in order to inflate the stomach ST with the aspirator 122 to reduce the pressure in the stomach ST, the distal end of the overtube 110 may be abutted to the stomach wall SW so absorb the space 123 partitioned by the stomach wall SW, including the overtube 110.

Fifth Embodiment

Figure 17:
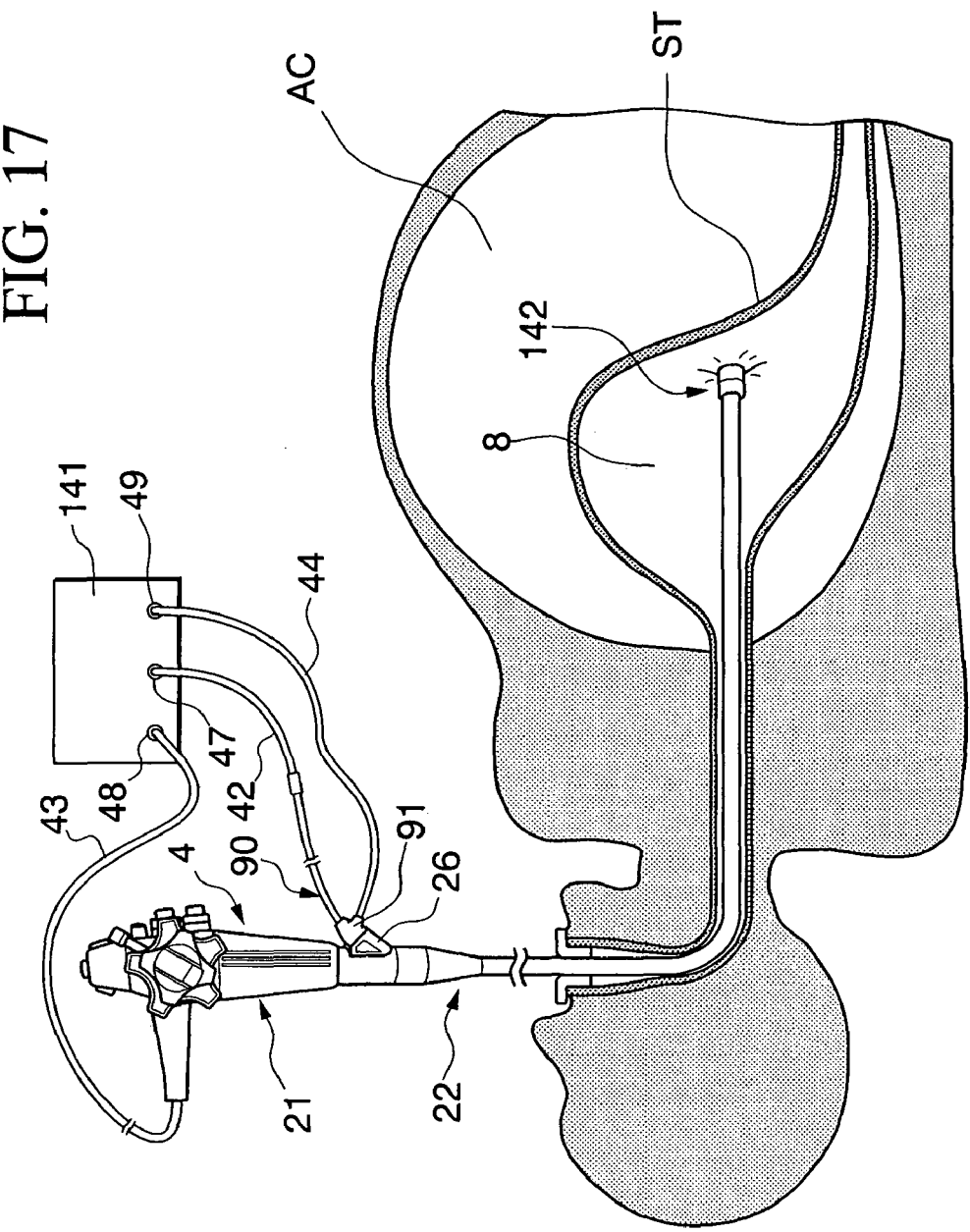
FIG. 17 is a diagram illustrating the air supply route according to another embodiment.

FIG. 17 shows a system of medical treatment in the present embodiment in a schematic view. An insufflation metal cap 47 of an air supply device 141 is connected to the lumen of the puncture needle 90. The metal cap 48 used in the stomach ST is connected to the air and water supply channel 34 of the endoscope 4. The tube 43 used for pressure measurement in the stomach ST is inserted into the port branched by the stopper 91 of the treatment tool insertion portion 26. Moreover, the air supply device 141 is configured to have an aspirator 122 attached downstream of the second flow rate sensor 74 in the air supply device shown in FIG. 6 instead of the second relief valve 73.

Figure 18:
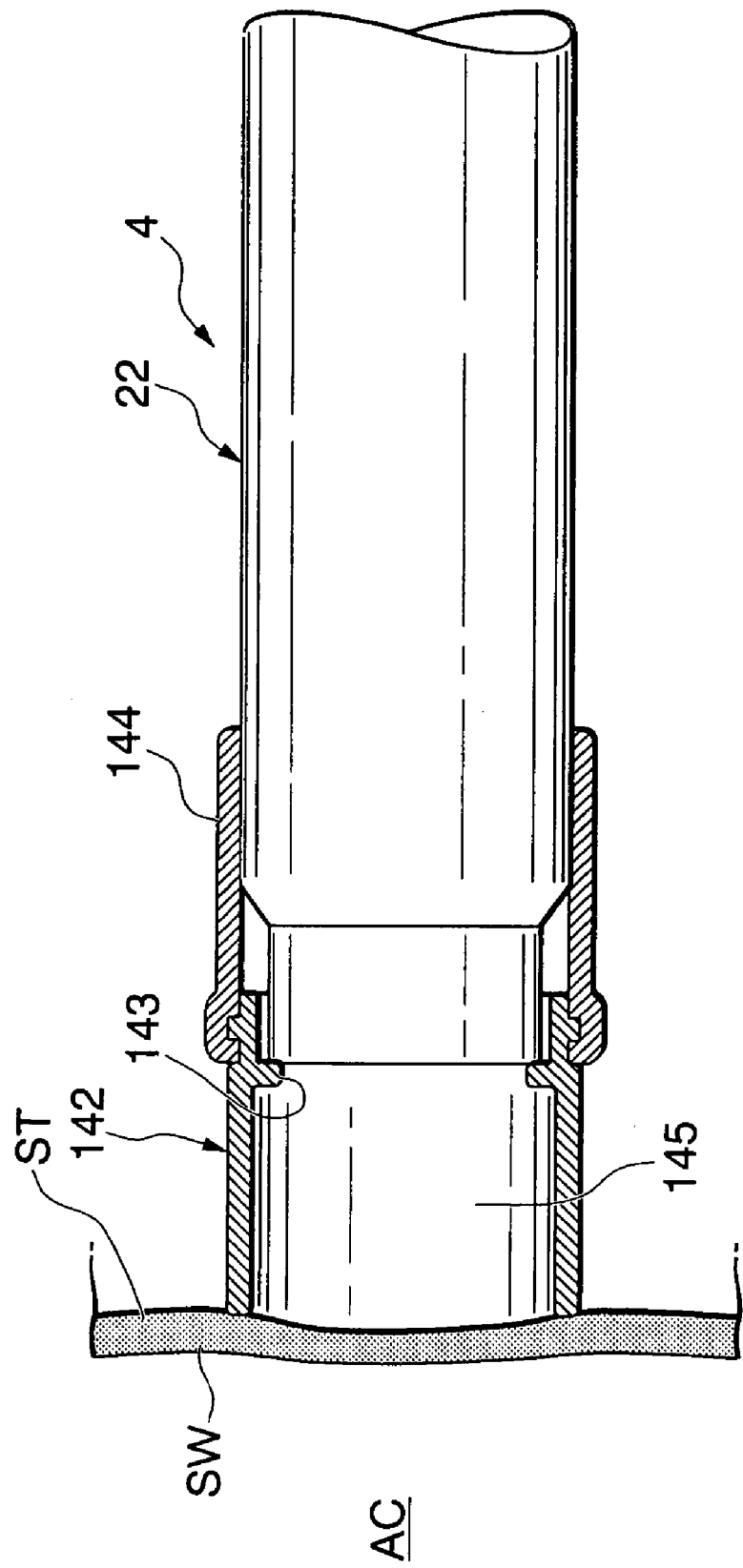
FIG. 18 is a cross-sectional diagram showing the structure of an end cover.

The endoscope 4 is provided with a distal end hood 142 mounted at the distal end of the insertion unit 22. As shown in FIG. 18, the distal end hood 142 has a cylindrical form, and is secured by a ring 144 in a state in which a ring like protrusion 143 within the periphery of the proximal end side presses against the distal end surface of the endoscope.

Conducted before medical operations are, inserting the endoscope 4 into the stomach ST, inflating the stomach ST by supplying air from the air supply device 141, and confirming that the target incision position. Conducted similarly to the fourth embodiment after confirming the target incision position are, abutting the distal end hood 142 to the stomach wall SW including the target incision position, advancing the puncture needle 90 in the distal end hood 142, and penetrating the puncture needle 90 into the stomach SW. Carbon dioxide gas is supplied from the air supply device 141 through the puncture needle 90 to insufflate the abdominal cavity AC. Next, the air supply device 141 closes the second solenoid-controlled valve 72, and actuates the aspirator 122. As shown in FIG. 19, the fluid in the space 145 defined by the stomach wall SW and the distal end hood 142 is absorbed through the aspiration channel 34 of the endoscope 4, and the stomach wall SW is pulled into the distal end hood 142 (the pressure of the space 145 enclosed by the distal end hood 142 is lower than the pressure within the abdominal cavity AC). Subsequently, the puncture needle 90 is removed, and a high-frequency knife is inserted through the operating channel 36.

As shown in FIG. 20, an opening is formed to the distal end 131 of the high-frequency knife 130 by incising the target open position. Since the pressure value Pss within the distal end hood 142 is lower than the pressure value Pa within the abdominal cavity AC, there is no outflow of liquid from the stomach ST side to the abdominal cavity AC. Necessary medical operation is executed by accessing the endoscope 4 to the abdominal cavity through the opening SO. The abdominal cavity AC is insufflated through the channel 34 of the endoscope 4. Upon the completion of the medical operation, the endoscope 4 is returned to the stomach ST. Since air is not delivered to the entire stomach ST, the pressure value Ps in the stomach ST is equal to or less than the pressure value Pa of the abdominal cavity AC, and there is no outflow of fluid from the stomach ST to the abdominal cavity AC.

According to the present embodiment without using an overtube, the same effects can be obtained as that of the fourth embodiment.

Although the present invention has been described with respect to its preferred embodiments, the present invention is not limited to the embodiments described above. The configuration of the present invention allows for addition, omission, substitution and further replacement without departing from the spirit and scope of the present invention. The present invention is not limited to the above descriptions but is limited only by the appended claims.

For example, a step may be conducted in which pressure is controlled inside the stomach ST based on the delivery of air only to the abdominal cavity AC, without inflating the stomach ST.

Figure 21:
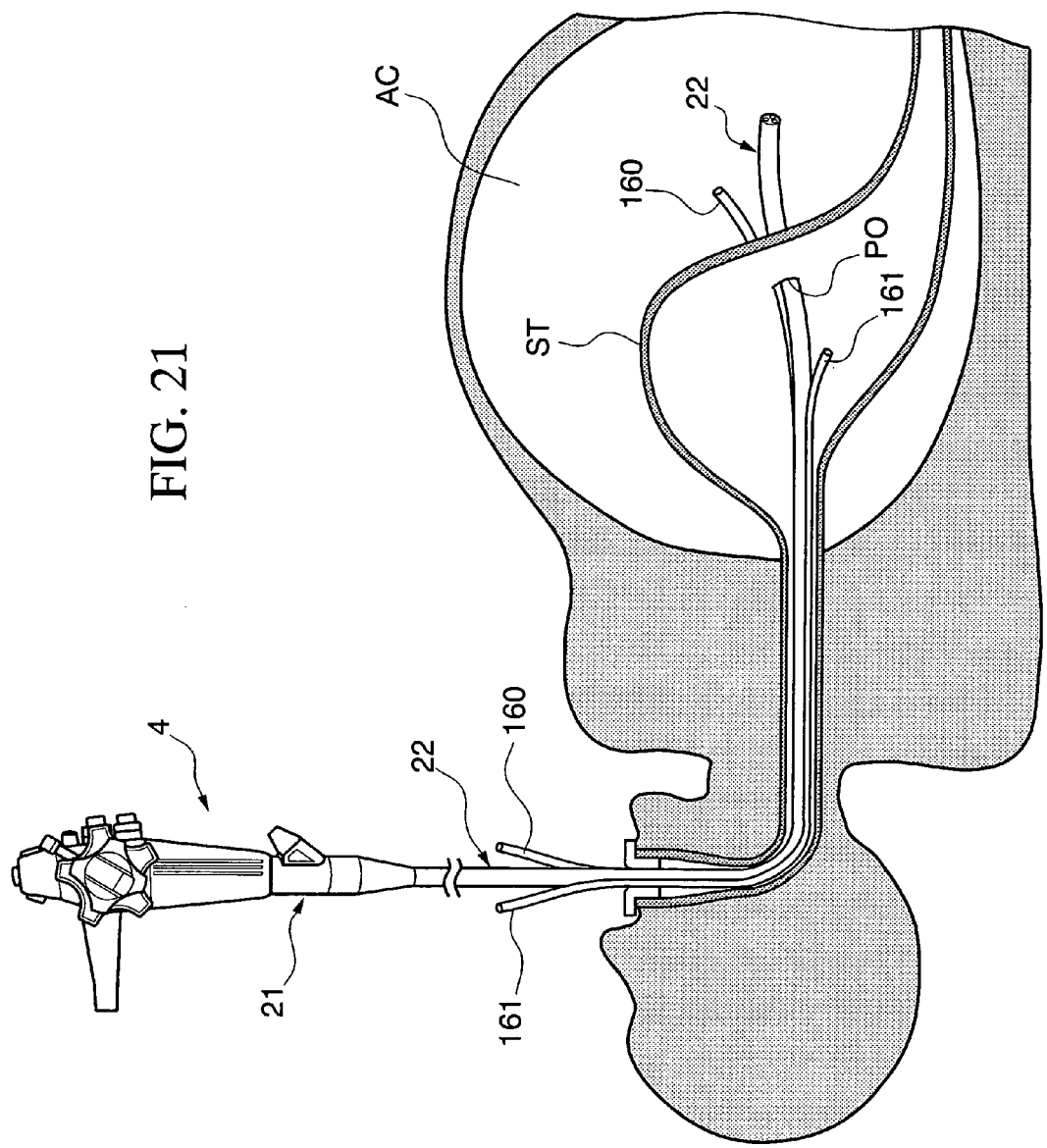
FIG. 21 is a diagram showing an embodiment in which a tube used for air expulsion is separately inserted into the endoscope.

As shown in FIG. 21, a insufflation tube 160 used for the abdominal cavity AC and an air supply tube 161 for delivering air to the stomach ST may be provided along the insertion unit 22 separate from the endoscope 4. The tube 160 having one or two lumens is connected to the insufflation metal cap 47 of the air supply device. The tube 160 is introduced to the abdominal cavity AC together with the insertion unit 22 and the endoscope 4 into the abdominal cavity AC through the stomach wall. Conducted before the insufflation and incision of the abdominal cavity AC are inserting the pneumoperitoneum needle 50 or the puncture needle 90 into the abdominal cavity AC and supplying air to the abdominal cavity AC. The tube 161 is inserted so that its distal end opening remains in the stomach ST. The same effects are obtained as those indicated above in cases where tubes 160 and 161 are inserted separately from the endoscope 4.

Figure 22:
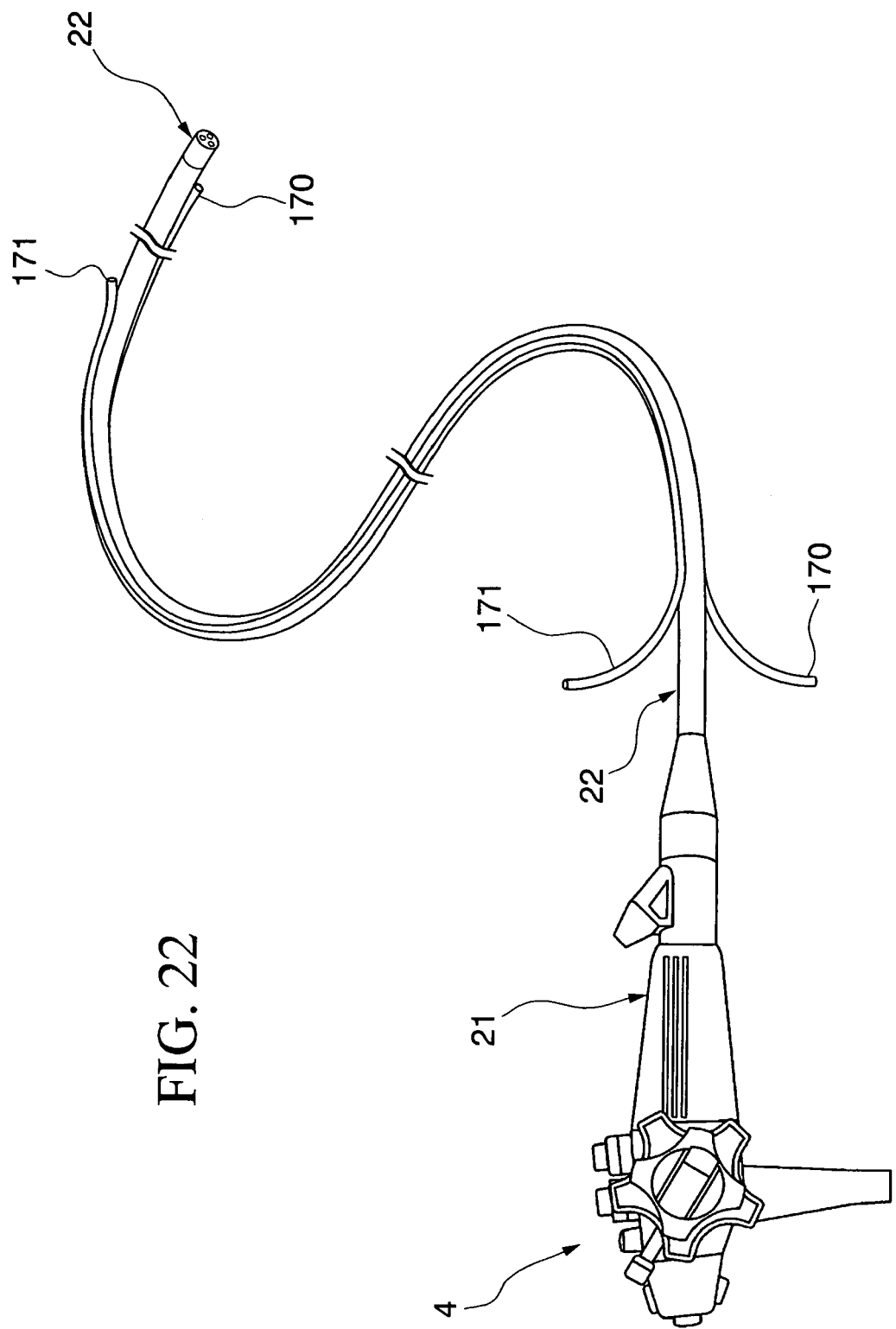
FIG. 22 is a diagram showing an embodiment in which there is an attached tube used for air exhaust delivery on the external side of the endoscope.

Furthermore, as shown in FIG. 22, air supply tubes 170 and 171 may also be fixed to the outer periphery of the insertion unit 22 of the endoscope 4. The tube 170 used for insufflation of the abdominal cavity AC includes one or two lumens and extends to the distal end of the insertion unit 22. The distal end opening of tube 171 which supplies air to the stomach ST is arranged close to the proximal end relative to the tube 171. The distal end of the tube 171 is positioned so that the tube 171 and the insertion unit 22 of the endoscope 4 can be inserted into the stomach ST; and the tube 171 will remain in the stomach ST when the endoscope 4 is introduced into the abdominal cavity through the stomach wall. The same effects as those indicated above can be obtained when the tubes 170 and 171 separated from the endoscope 4 are used.

As shown in FIG. 23, an air supply tube 181 used for supplying air to the stomach ST may also be fixed along the outer periphery of the overtube 110 in the structure having lumens i.e., the overtube 110 used for insufflation of the abdominal cavity AC. The tube 181 also need not be fixed to the overtube 110. In addition, insufflation may be conducted through an attached lumen used for air supply within the overtube 110. Moreover, the port 113 is arranged further to the distal end side from an airtight valve 182. Conducted before the insufflation and incision of the abdominal cavity AC are inserting the pneumoperitoneum needle 50 or the puncture needle 90 into the abdominal cavity AC and supplying air to the abdominal cavity AC.

Figure 25:
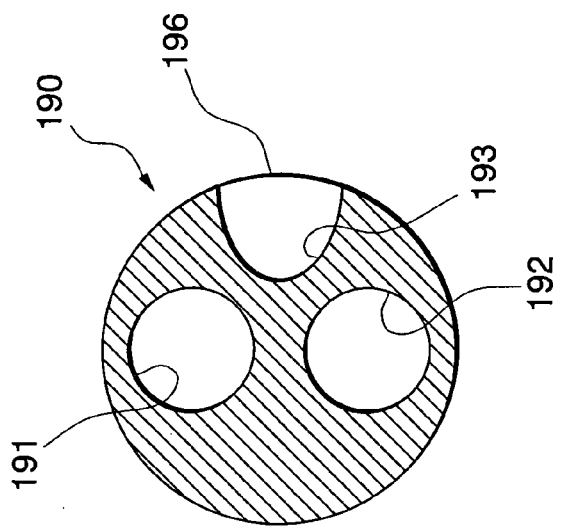
FIG. 25 is a cross-sectional diagram along the line XXV-XXV of FIG. 24.
Figure 24:
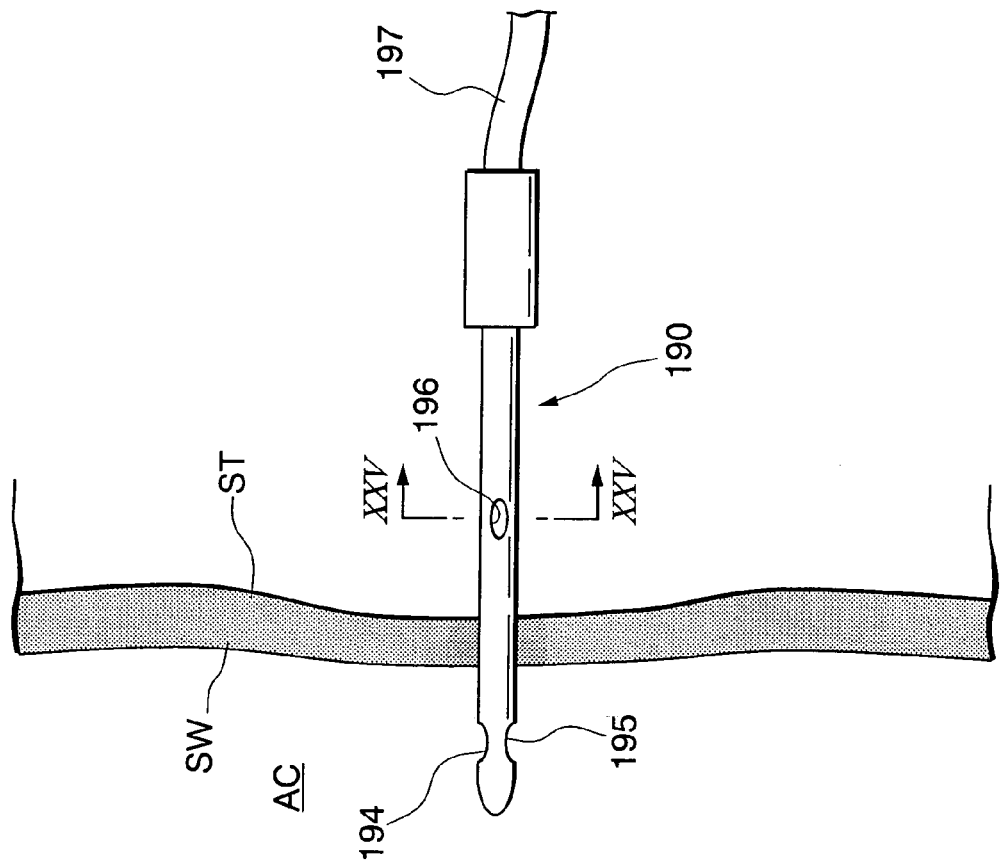
FIG. 24 is a view showing an pneumoperitoneum needle inserted in a stomach.

An intragastric pneumoperitoneum needle 190 may be used as shown in FIG. 24 and FIG. 25. The intragastric pneumoperitoneum needle 190 includes three lumens 191, 192 and 193. Provided on the outer circumferences of the lumen 191 used for insufflating the abdominal cavity and the lumen used for exhausting air therefrom are openings 194 and 195 formed in the vicinity of sharp end of the intragastric pneumoperitoneum needle 190. The third lumen 193 for air delivery and evacuation to and from the stomach has an opening 196 on the outer circumference in the middle of the longitudinal direction, e.g., toward the proximal end. The tube 197 includes three independent lumens. The lumens 191 to 193 each of the intragastric pneumoperitoneum needle 190 are connected to each independent lumens. The insufflation lumen 191 is connected to insufflation metal cap 47 of the air supply device. The air evacuation lumen 192 is connected to an aspirator which is not shown. The lumen 193 for air delivery and evacuation to and from the stomach is connected to the metal cap 47 used within the air supply device in the stomach ST.

The intragastric pneumoperitoneum needle 190 separated from the endoscope 4 is inserted into the stomach ST through the operating channel 36 of the endoscope 4 so that the needle 190 penetrates the stomach wall SW and the opening 196 of the lumen 193 remains in the stomach ST. Air is supplied from the lumen 19 used for abdominal cavity air supply so as to insufflate the abdominal cavity AC. Air is supplied next into the stomach ST through the lumen 193 for air delivery and evacuation to insufflate the stomach ST. The lumen 193 for air delivery and evacuation is released to the atmosphere to adjust the pressure in the stomach ST. In addition, smoke produced when using a high-frequency treatment tool in the abdominal cavity AC is exhausted from the air evacuation lumen 192 for the stomach of the pneumoperitoneum needle 190. The single pneumoperitoneum needle 190 can be of compatible use, e.g., air supply, air expulsion, and pressure adjustment.

A pipe path for inflating a hollow organ and a pipe path for insufflation of the abdominal cavity AC may be inserted from different natural orifices. For example, the endoscope may be inserted from the patient's mouth while the tube used for insufflation may be inserted from the anus, or air may be supplied to the abdominal cavity AC through the wall of the large intestine.

The device needed for performing a desired manipulation is not limited to the endoscope comprising the observation device and the work channel described in the above embodiments. For example, a device may be used (hereunder, called a treatment device for convenience) comprising a treatment portion for performing a desired treatment provided on the distal side of the insertion portion to be inserted into the body, and an operation portion capable of operating this treatment portion from outside of the body. In this case, a medical operation is accomplished while making observations with an observation device which can be swallowed, such as a capsule endoscope.

An example will be explained next in which the gas in the hollow organs is exhausted to the atmosphere through the overtube according to the present embodiment.

Figure 26:
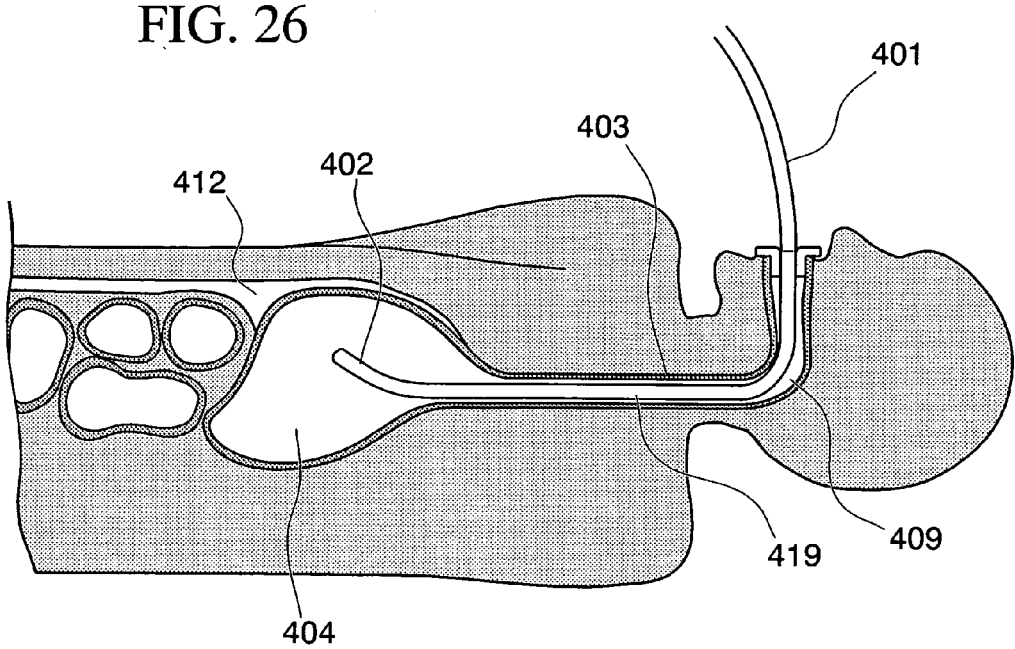
FIG. 26 is a side-sectional schematic view of the human torso illustrating an endoscope passing through the oropharynx and esophagus into the stomach.

Transgastric endoscopic exploration and transgastric endoscopic surgery are newly developing techniques for observing, obtaining biopsies and performing surgery in the peritoneal cavity. The procedure is typically performed as follows. As illustrated in FIG. 26, after prepping the patient, a flexible endoscope 419 with a proximal end 401 and a distal end 402 is passed through the mouth, oropharynx 409 and esophagus 3 into the stomach 404. The stomach is insufflated with gas, typically air, in order to expand the stomach and smooth out any folds in the stomach wall and to create an interior working space in the stomach ST for manipulating the endoscope and locating an ideal site for incising the wall of the stomach.

Figure 27:
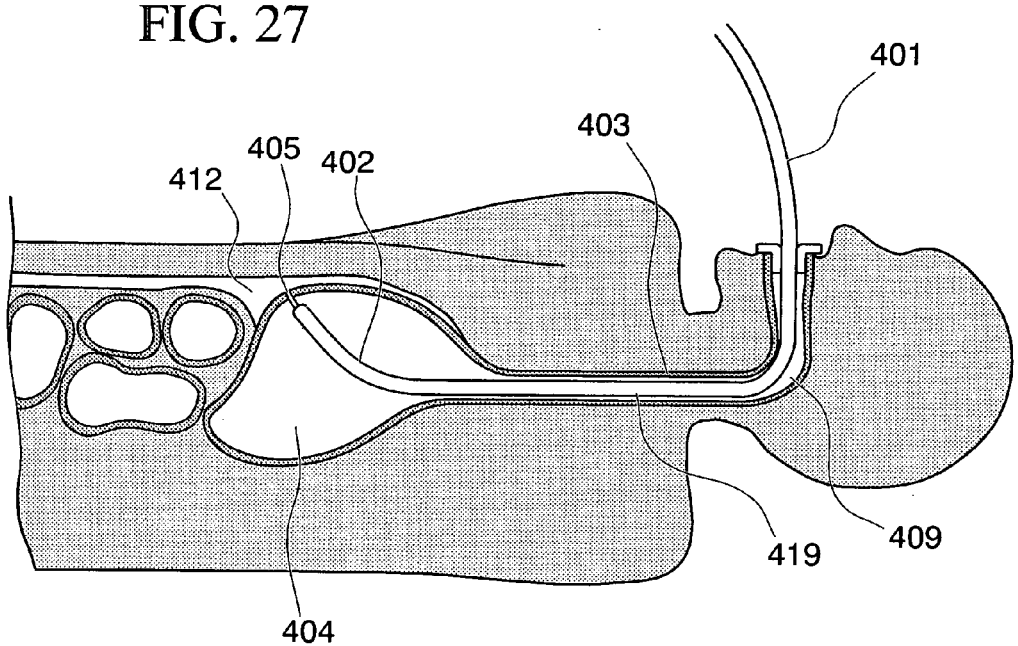
FIG. 27 is a side-sectional schematic view of the human torso illustrating an endoscope employing a needle electrode at its distal tip to make an incision in the wall of the stomach.
Figure 28:
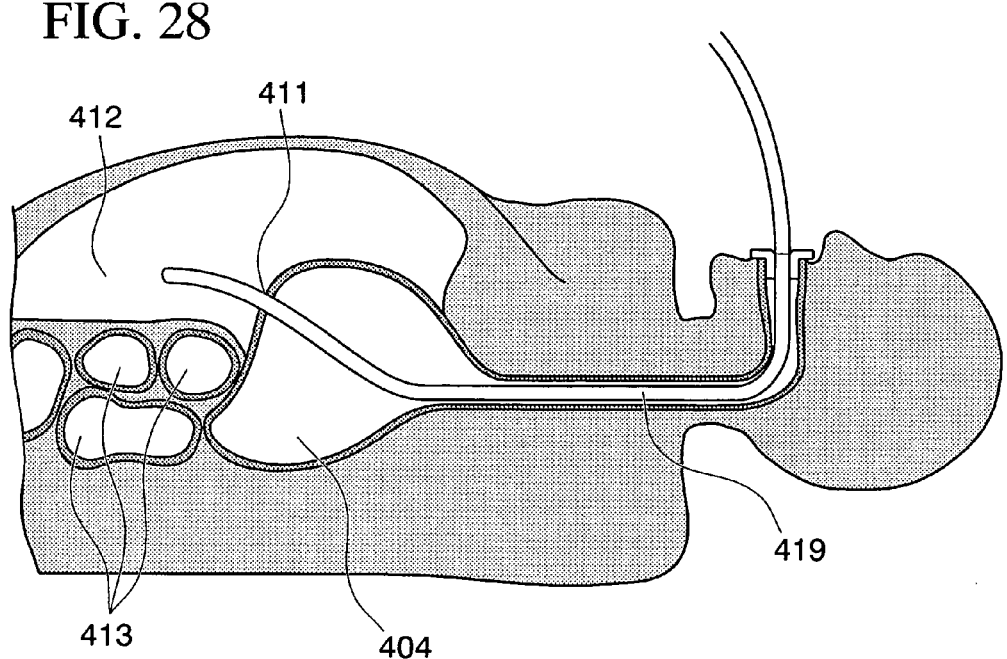
FIG. 28 is a side-sectional schematic view of an endoscope passing through an incision in the wall of the stomach and entering the lumen of the abdominal cavity.

With the stomach inflated with gas, the operator then chooses a site on the stomach wall to make a full thickness incision of the stomach wall. Depending upon which abdominal organs the operator desires to inspect, biopsy or perform surgery on, the operator may select to incise the posterior wall of the stomach, the anterior wall of the stomach, or other suitable location on the stomach wall. The incision of the stomach wall can be made with a variety of techniques. As illustrated in FIG. 27, one method is to employ a retractable needle-tipped electrode 405 through the endoscope 419 using radio frequency (RF) cutting or coagulating current to cut through the tissue of the stomach wall, while providing a hemostatic effect on the incised tissue. In one variant of the procedure, the length of the incision is selected so that it creates an incision or opening in the stomach wall of the approximate diameter, or slightly less than the diameter, of the endoscope. As illustrated in FIG. 28, if the incision 411 is correctly sized, when the endoscope 419 is passed through the wall of the stomach 404 and enters the lumen of the abdominal cavity 412, the tissue of the stomach wall will create a gas-tight seal around the outer surface of the endoscope.

Figure 29:
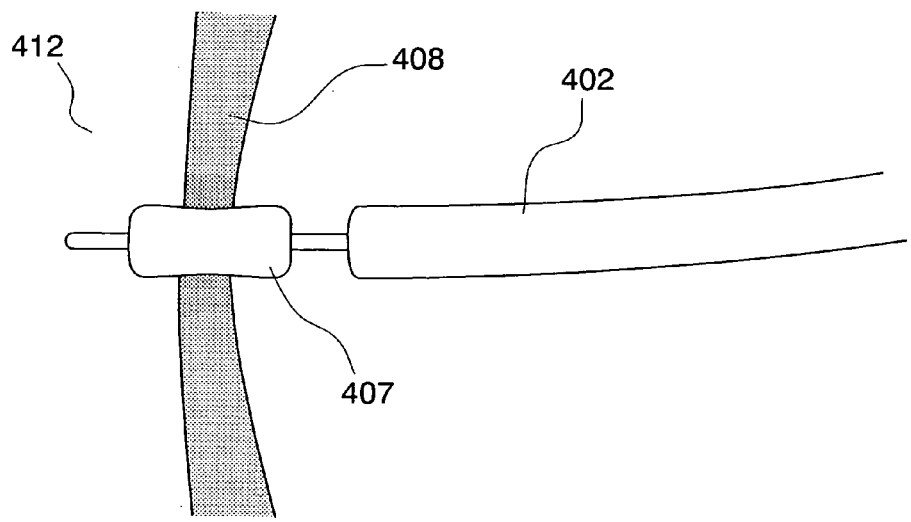
FIG. 29 is a schematic of a dilation balloon placed through an endoscope and positioned in an incision in the wall of the stomach in order to dilate the small incision in the stomach.

In another variant of the procedure a small hole is made in the wall of the stomach. As illustrated in FIG. 29, a balloon dilator 407 is then passed through this small hole, positioned such that it is approximately centered in the stomach wall 408, and inflated with sufficient pressure to dilate the small hole in the stomach to a diameter that will allow passage of the distal end of the endoscope 402. If the opening is dilated to the correct size, it will allow the distal tip 402 of the endoscope to slip through the stomach wall into the lumen 412 of the abdominal cavity, while at the same time creating a gas-tight seal between the outer surface of the endoscope and the stomach wall.

Figure 30:
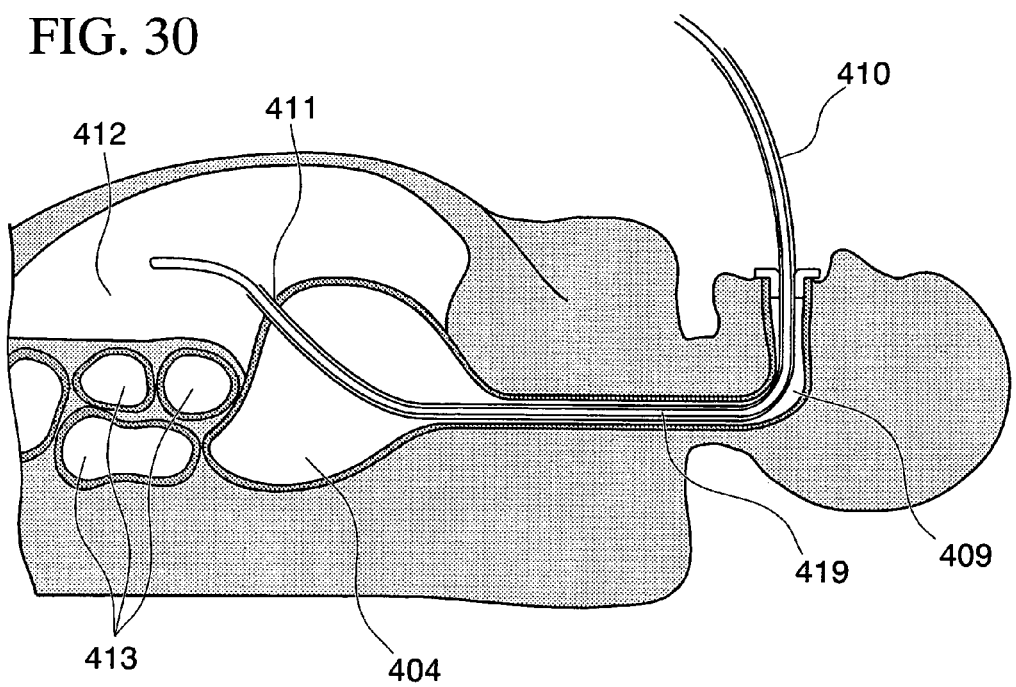
FIG. 30 is a side-sectional schematic view of the human torso illustrating an endoscope and overtube passing into the lumen of the abdominal cavity.

While the endoscope may be used by itself, there are advantages to passing the endoscope through an overtube. As FIG. 30 illustrates, one advantage of an overtube 410 is that it provides smooth passage of the endoscope through the oropharynx 409 and through the incision 411 in the stomach wall. Guided passage of the endoscope along this route is very useful if the endoscope is going to be repeatedly withdrawn and reinserted into the patient.

Another advantage is that the overtube can be modified to allow it to control the amount and pressure of gas used to insufflate the stomach—a benefit which is the object of the present invention.

If an overtube is used (FIG. 30), the length of the gastric wall incision 411 should be made such that the gastric wall forms a gas-tight seal around the outer surface of the overtube 410 through which the endoscope 419 is passed. This tight seal between the overtube and the stomach wall serves several purposes. In the first instance it will prevent the leakage of any stomach contents into the lumen 412 of abdominal cavity while the endoscope is being manipulated in the lumen of the abdominal cavity. In the second instance, it will create two gas-tight compartments within the body. After the incision is made in the stomach wall, gas can flow freely between the interior of the stomach 404 and the intraperitoneal space 412. As a result of the communication between these two spaces it is impossible for the endoscopist to independently insufflate only the stomach 404 or only the intraperitoneal space 412. However, once the endoscope is passed through the wall of the stomach and creates a gas-tight seal between the endoscope and the stomach wall, two independent air spaces are created. The first is the interior of the stomach 404, along with the small intestines 413 which are joined to the stomach at the region of the pylorus 406. (See FIG. 32) The second is the intraperitoneal space 412 which is now isolated from communication with the stomach interior 404 since the incision 411 in the stomach wall is tightly plugged with the overtube 410. In such a condition, the amount of gas pressure and the degree of expansion of these two spaces can be controlled independently.

Figure 31:
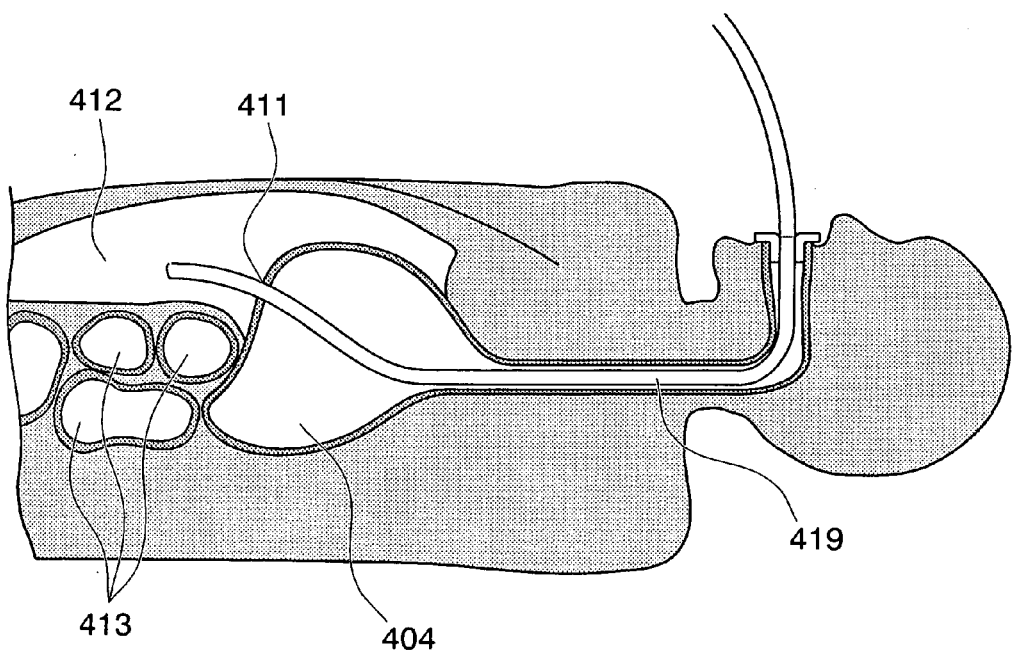
FIG. 31 is a side-sectional schematic of the human torso similar to FIG. 28, but illustrating that expansion of the stomach and intestines reduces the size of the lumen of the abdominal cavity.

During the initial part of the procedure it is important to insufflate the stomach with gas to create an adequate working space in the stomach ST interior for the endoscopist to choose an incision site and endoscopically create the incision. However, once the incision in the stomach wall has been made and the endoscope has been passed into the intraperitoneal space, it is disadvantageous to have an insufflated stomach. On the one hand, as shown in FIG. 31, the expanded stomach 404 protrudes into the lumen 412 of abdominal cavity reducing the volume of the peritoneal cavity and restricting the endoscopist's ability to manipulate the endoscope and access other organs in the intraperitoneal space. On the other hand, the expanded stomach may obscure observation and manipulation of other abdominal organs, making the procedure less effective and more difficult. A second disadvantage of having high gas pressure in the stomach is that this gas will pass through the pylorus 406 and insufflate and expand the small intestines 413 as well. When the small intestines 413 are expanded with gas they also reduce the available working space within the lumen of the abdominal cavity 412 and prevent the endoscopist from effectively observing and operating on other abdominal organs. Therefore, while initial insufflation of the stomach is desirable for choosing an incision site and making an incision in the stomach wall, once the endoscope is passed through the stomach wall and is operating within the lumen of the abdominal cavity, it is very advantageous to be able to remove gas from the stomach interior in order to deflate it and to prevent the passage of gas from the stomach to the small intestines. FIG. 28 illustrates the large intraperitoneal space 412 created when the stomach 404 and small intestines 413 are deflated, while FIG. 31 illustrates how an expanded stomach 404 and expanded intestines 413 reduce the size of the intraperitoneal space 412.

The object of the present invention is to control the insufflation of the stomach and the small intestines during transgastric endoscopic observation and/or surgery. To be more specific, the devices described allow for the decompression of the stomach and small intestines at will, and/or the prevention of gas flowing into the small intestine during the transgastric endoscopic procedure.

FIGS. 32A and 32B show one embodiment of an overtube 415 that provides stomach insufflation control. The overtube 415 is passed through the patient's mouth and oropharynx (not shown) through the esophagus 403 into the patient's stomach 404. An endoscope 419 is passed through this overtube 415 and through an opening 411 in the stomach wall. A gas-tight seal between the stomach wall and the outer surface of the endoscope 419 separates the gas compartment of the lumen of the abdominal cavity from the gas compartment of the interior of the stomach and intestines. A gas-tight seal 416 between the endoscope 419 and the overtube 415 at the proximal end 417 of the overtube prevents any gas from the stomach 404 from leaking out of the proximal end of the overtube. An intraluminal space 418 exists between the interior surface of the overtube 415 and the exterior surface of the endoscope 419. The intraluminal space 418 is contiguous with the interior space of the stomach 404 and the intestines 413 and the lumen of a gas port 420 on the proximal end 417 of the overtube 415. The gas port 420 enables gas to be added or removed from the stomach 404 and intestines 413 during the procedure.

Figures 33A, 33B:
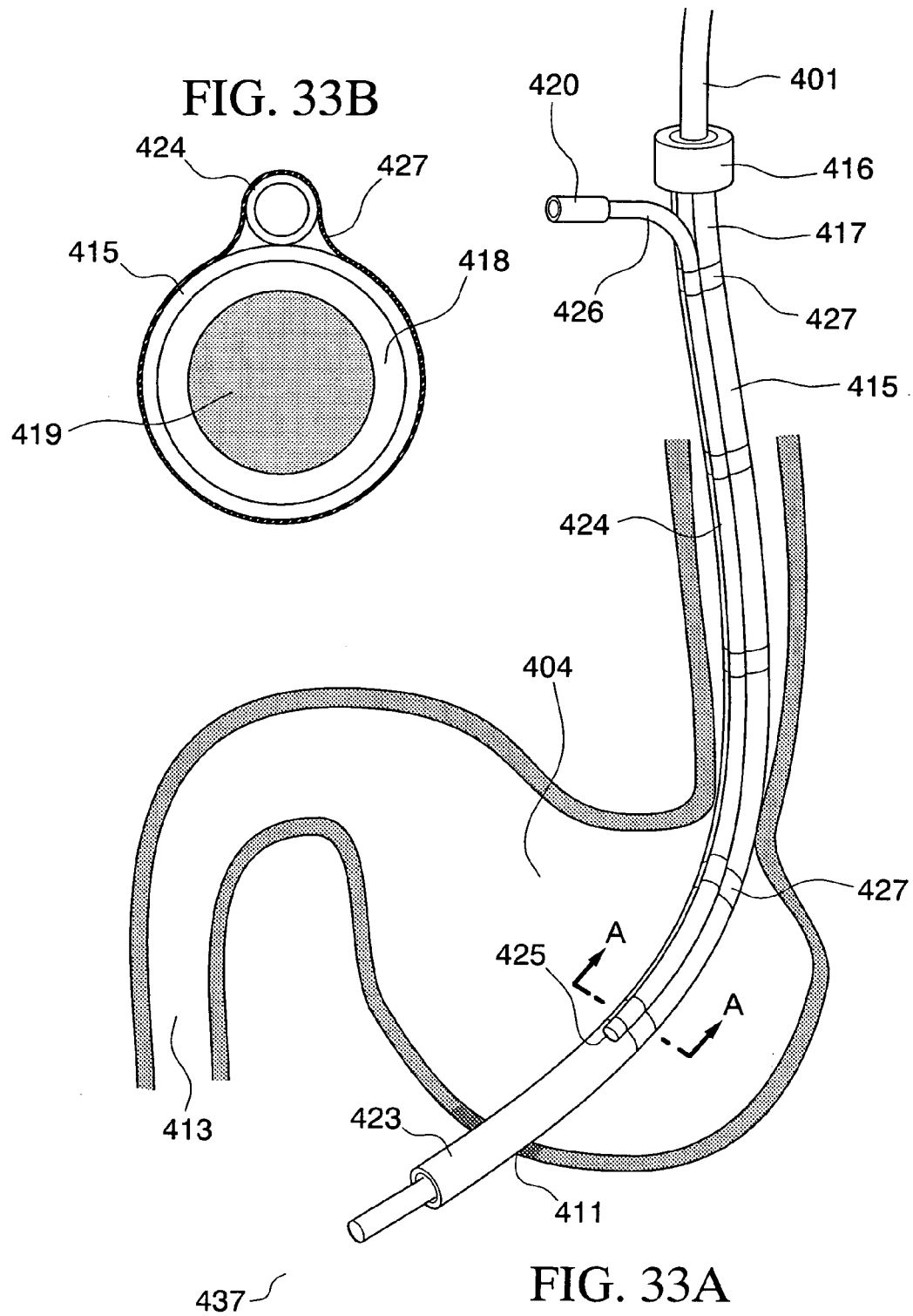
FIG. 33B illustrates a sectional view taken along line A-A in FIG. 33A.

FIGS. 33A and 33B illustrate another embodiment of the present invention. In the present embodiment the overtube 415 is inserted through an incision 411 in the stomach wall with the distal end of the overtube 423 residing in the intraperitoneal space 412. The dimension of the stomach wall incision 411 is such that a gas-tight seal is created between the stomach wall and the distal tip 423 of the overtube. This seal separates the intraperitoneal air space 412 from the air space within the interior of the stomach 404 and intestines 413. A tube 424 with lumen is placed along the outer surface of the overtube. The distal end of this lumen opens into the interior of the stomach 404. The proximal end 426 of this lumen connects to a gas port 420 outside of the patient and allows gas to be added to or removed from the interior of the stomach 404 and small intestines 413. An air tight seal 416 between the proximal end 417 of the overtube and the proximal end 419 of the endoscope prevents gas within the intraperitoneal space from escaping up the intraluminal space and out the proximal end 417 of the overtube. In the present embodiment, gas pressure in the stomach ST and the intestines can be controlled by adding or removing gas via the gas port 420 on the tube 424 with lumen. The tube 424 with lumen is securely attached to the overtube 415. One means of attachment is the use of adhesive tape 427, although many other means are available.

In the embodiment illustrated in FIGS. 34A and 34B, the lumen 428, which is used to add or remove gas from the stomach 404, has been extruded as an integral part of the wall of the overtube 415. FIG. 34A illustrates a cross-section of the overtube 415 at A-A, illustrating that the gas lumen 428 and the overtube 429 lumen share a common wall 430. The distal end of the gas lumen 428 opens into the stomach. The proximal end of the gas lumen communicates with the gas port 420 via connecting tube 434. Gas injected into or withdrawn from the gas port 420 will therefore add or remove gas respectively from the stomach 404 and intestines 413.

Figure 35B:
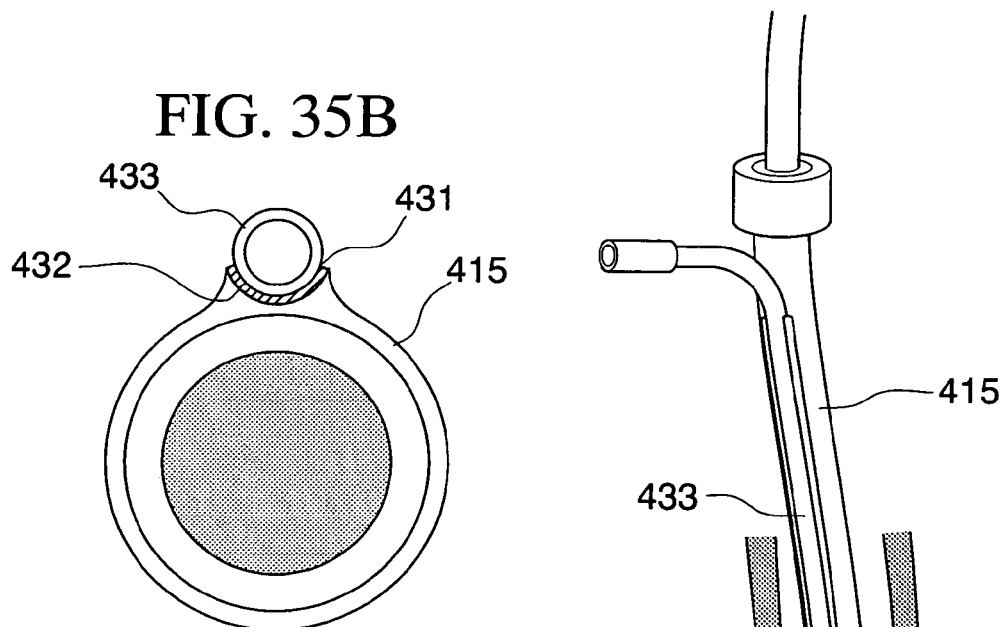
FIG. 35B illustrates a sectional view taken along line A-A in FIG. 35.
Figure 35A:
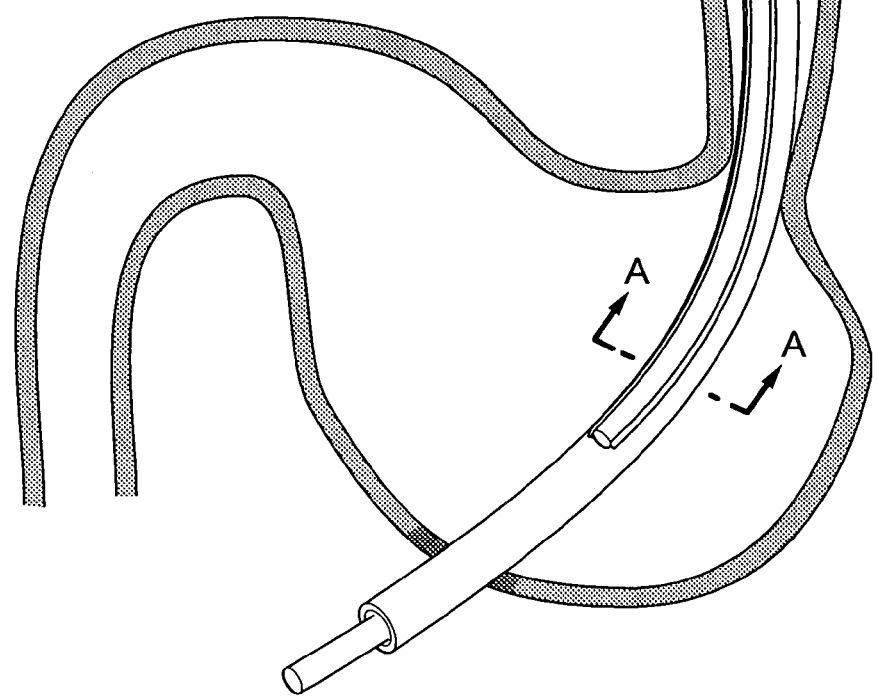
FIG. 35A illustrates an isometric view of an overtube according to a fourth embodiment, where the overtube is shown together with an endoscope, and the overtube and the endoscope are inserted through an incision in the stomach.

Alternatively, as illustrated in FIGS. 35A and 35B, the overtube 415 could be extruded with a channel 432 designed to accept the gas lumen 433, which is then adhered to the overtube 415 with an adhesive. Reference numeral 431 indicates an adhesive.

Figure 36B:
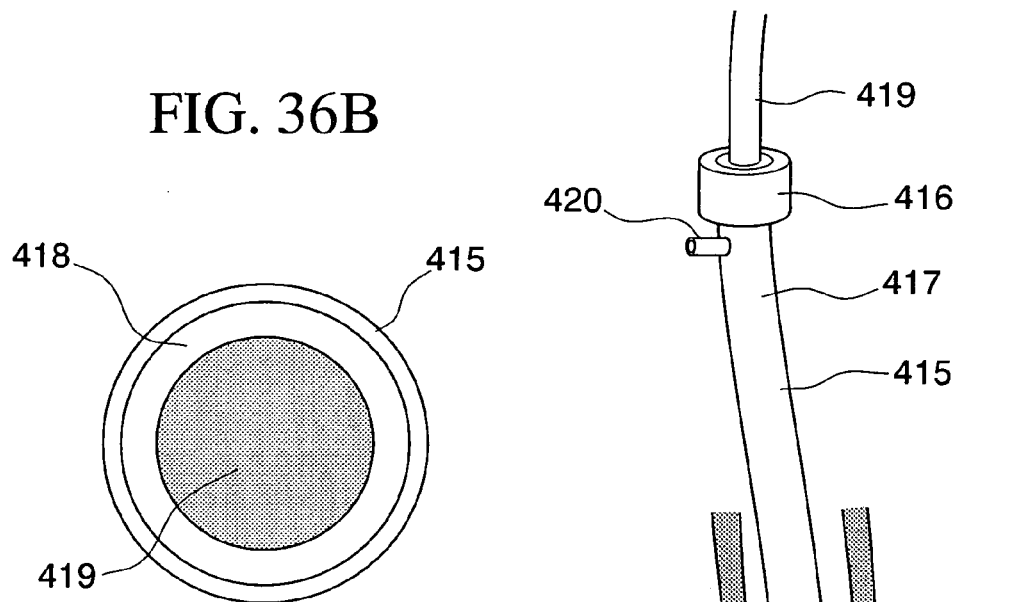
FIG. 36B illustrates a sectional view taken along line A-A in FIG. 36A.
Figure 36A:
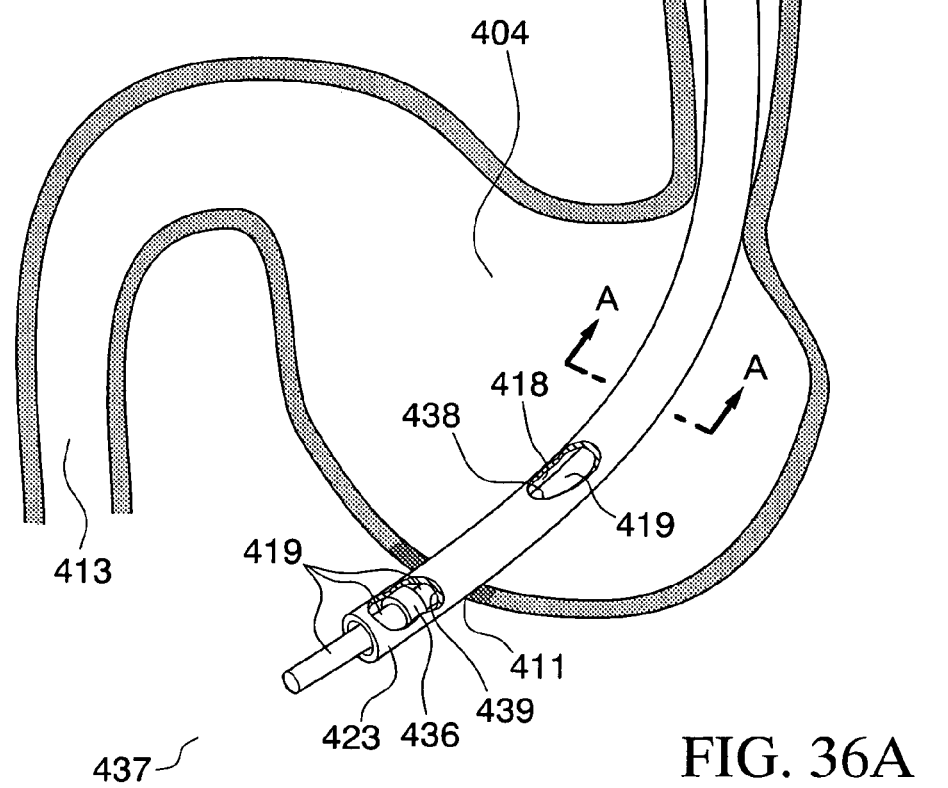
FIG. 36A illustrates an isometric view of an overtube according to a fourth embodiment, where the overtube is shown together with an endoscope, and the overtube and the endoscope are inserted through an incision in the stomach. A cutaway of the distal end of the overtube shows a view of a gas seal between the overtube and the endoscope. An opening in the wall of the overtube allows gas flow between the stomach and the lumen of the overtube.

FIGS. 36A and 36B illustrate another embodiment of the present invention. In the present embodiment the overtube 415 is inserted through an incision 411 in the stomach wall with the distal end 423 of the overtube residing in the intraperitoneal space 437. The dimension of the stomach wall incision 411 is such that a gas-tight seal is created between the stomach wall and the distal end 423 of the overtube. In addition, the distal end 423 of the overtube contains a mechanical gas-tight seal between the distal end 423 of the overtube and the exterior surface of the endoscope 419. This gas-tight seal 436 is shown in a cutaway view 439 of the FIG. 36A. The gas-tight seal 436 separates the intraperitoneal air space 437 from the intraluminal air space 418 and the air space of the interior of the stomach 404 and intestines 413. An opening 438 in the wall of the overtube 415 allows the air space of the interior of the stomach 404 and intestines 413 to communicate with the intraluminal air space 418. The intraluminal air space 418 also communicates with the lumen of an air port 420 on the proximal end 417 of the overtube 415. A gas-tight seal 416 at the proximal end 417 of the overtube prevents gas in the intraluminal space 418 from escaping out of the proximal end of the overtube. By adding or removing gas via the air port 420, the gas pressure in the stomach ST 404 and the small intestines 413 can be controlled, independently of the gas pressure within the lumen of the abdominal cavity 437. Both the gas-tight seal 416 at the proximal end 417 of the overtube and the gas-tight seal 436 at the distal end 423 of the overtube allow easy sliding passage of the endoscope 419 through the overtube 415.

In each of the embodiments illustrated in FIGS. 32A to 36B, passage of gas through the air port 420 can be controlled in a variety of means. One means is to leave the air port 420 open at all times to allow gas in the stomach ST and intestines to escape from the patient. Since both the surrounding abdominal organs and the intraperitoneal pressure constantly act to compress the stomach and intestines, venting the stomach and intestines to the atmosphere will allow them to expel much of the free gas within these organs, thereby reducing their protrusion into the intraperitoneal space.

Figure 37:
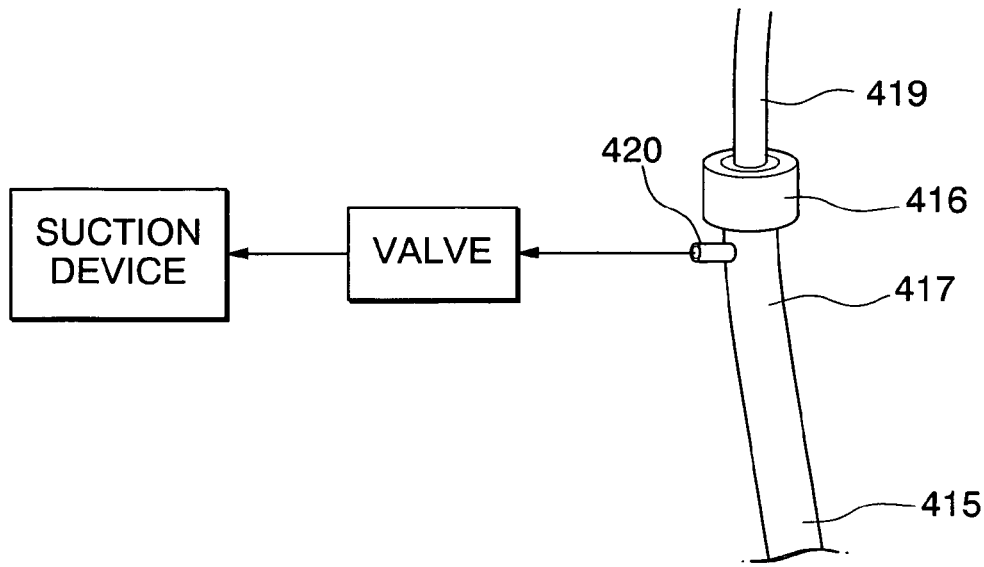
FIG. 37 is a schematic of the connection of the overtube to a suction device. The suction device removes gas from the lumen of the overtube. A valve between the two devices controls the application of suction to the overtube.

As illustrated in FIGS. 37A and 37B, another means of controlling the gas pressure within the interior of the stomach and intestines is to attach a valve to the gas port 420 which is opened and closed under the control of the endoscopist. Typically the gas port 420 would be connected to a suction device. Therefore, opening the valve will apply suction to the intraluminal space in the overtube and will remove gas from the interior of the stomach and intestines.

Alternatively, the air port could be connected to a gas source such as a pump or compressed gas source. In this case, opening the valve would add gas to the interior of the stomach and intestines.

Figure 38:
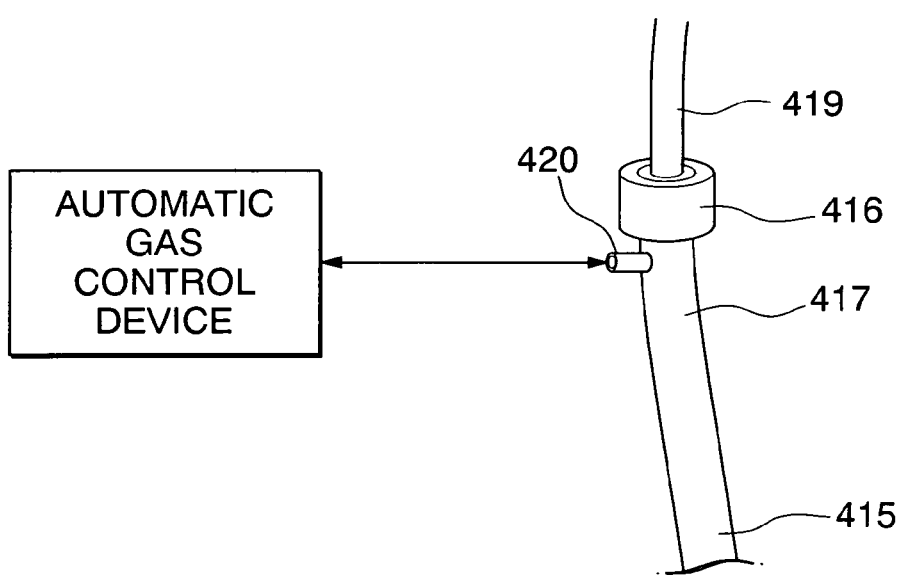
FIG. 38 is a schematic of an alternative embodiment illustrating that if an automatic gas control device is connected to the overtube, it can both inject gas into and remove gas from the overtube lumen.

As illustrated in FIGS. 38A and 38B, another means of controlling the gas pressure within the interior of the stomach and intestines is to attach the gas port 420 to an automatic gas control device. This automatic controller will accurately maintain the gas pressure within the interior of the stomach and intestines to a preset value by either adding or removing gas as necessary, or will automatically remove all gas in the stomach ST and intestines by applying suction to the gas port, under the control of the endoscopist.

The gas-tight seal between the endoscope and the overtube can be constructed using several alternative methods commonly known in the art. One of these methods is to employ closed-cell foam rubber to make a compressible seal around the outer surface of the endoscope. Another commonly used method is to employ a flexible diaphragm made of rubber, polymer or other material, with a central hole through which the endoscope is passed. This central hole expands slightly as the endoscope is placed through it, creating an airtight seal. Other methods of sealing between the endoscope and the overtube are known to those working in this field. Any type of gas-tight seal that allows the endoscope to be advanced through, and to be withdrawn from, the overtube is suitable.

Although room air is typically used for insufflation during endoscopy of the stomach, insufflation with $CO_2$ has the advantage that it is absorbed by the body quicker than air. Therefore if $CO_2$ is used for insufflating the stomach, and during the procedure $CO_2$ gas travels into the small intestines thereby expanding them, this $CO_2$ will be absorbed at a faster rate than if room air had been used for the insufflation. This inherent higher absorption rate of $CO_2$ gas will speed the deflation of the small intestines, making more room in the intraperitoneal space and improving the ease of performing the procedure.

What is claimed is:

1. A natural orifice medical operation, comprising:
introducing a first flow path into the abdominal cavity;
introducing a second flow path into a hollow organ from a natural orifice of a living body;
performing a pressure control so that a pressure in the hollow organ is lower than a pressure of the abdominal cavity by using of the first flow path and the second flow path;
forming an opening in a wall of the hollow organ from the inside of the hollow organ when the pressure in the hollow organ is equal to or less than the pressure in the abdominal cavity, in the step of performing a pressure control; and
inserting a device for performing a medical operation through the opening.

2. The method for accessing an abdominal cavity according to claim 1, wherein the first flow path is percutaneously introduced into the abdominal cavity.

3. The method for accessing an abdominal cavity according to claim 1, wherein the performing the pressure control comprises:
performing insufflation in the abdominal cavity by using the first flow path; and
releasing gas in the hollow organ by using the second flow path until the pressure in the hollow organ is equal to or less than the pressure in the abdominal cavity.

4. The method for accessing an abdominal cavity according to claim 3, wherein the gas is supplied to the hollow organ prior to releasing the gas in the hollow organ.

5. The method for accessing an abdominal cavity according to claim 1, wherein the first flow path is penetrated through the hollow organ to be introduced into the abdominal cavity after the first flow path is inserted into the hollow organ from the natural orifice of the living body.

6. The method for accessing an abdominal cavity according to claim 5, wherein the performing the pressure control comprises:

performing insufflation in the abdominal cavity by using the first flow path; and releasing gas in the hollow organ by using the second flow path until the pressure in the hollow organ is equal to or less than the pressure in the abdominal cavity.

7. The method for accessing an abdominal cavity according to claim 6, wherein the gas is supplied to the hollow organ prior to releasing the gas in the hollow organ.

8. The method for accessing an abdominal cavity according to claim 1, wherein the introducing the second flow path comprises inserting an overtube which functions as an insertion guide of a device having an insertion portion inserted into the living body such that a distal end of the second flow path is retained in the hollow organ.

9. The method for accessing an abdominal cavity according to claim 8, wherein the performing the pressure control comprises:

performing insufflation in the abdominal cavity by using the first flow path; and releasing gas in the hollow organ by using the second flow path until the pressure in the hollow organ is equal to or less than the pressure in the abdominal cavity.

10. The method for accessing an abdominal cavity according to claim 9, wherein the gas is supplied to the hollow organ prior to releasing the gas in the hollow organ.

11. The method for accessing an abdominal cavity according to claim 1, wherein the introducing the second flow path comprises pressing a cylindrical body communicating with the device against the wall of the hollow organ, and the performing the pressure control comprises absorbing a fluid in the space formed between the cylindrical body and the inner wall of the hollow organ.

12. The method for accessing an abdominal cavity according to claim 3, wherein the performing the pressure control further comprises releasing the hollow organ to an atmosphere.

13. The method for accessing an abdominal cavity according to claim 7, wherein the performing the pressure control further comprises releasing the hollow organ to an atmosphere.

14. The method for accessing an abdominal cavity according to claim 9, wherein the performing the pressure control further comprises releasing the hollow organ to an atmosphere.

15. A natural orifice medical operation comprising:

introducing a first flow path into an abdominal cavity;

introducing a second flow path into the hollow organ from a natural orifice of a living body;

performing a pressure control using the first flow path and the second flow path so that a pressure in the hollow organ is lower than a pressure of the abdominal cavity; and withdrawing a device, which is inserted from the natural orifice of the living body and is introduced into the abdominal cavity through an opening formed in the hollow organ, from the abdominal cavity, in a state in which, by performing a pressure control, the pressure in the hollow organ is made lower than the pressure in the abdominal cavity.

* * * * *